United States Patent
Chaudhary et al.

(10) Patent No.: US 11,663,790 B2
(45) Date of Patent: May 30, 2023

(54) DYNAMIC TRIGGERING OF AUGMENTED REALITY ASSISTANCE MODE FUNCTIONALITIES

(71) Applicant: Optum, Inc., Minnetonka, MN (US)

(72) Inventors: Kartik Chaudhary, Bangalore (IN); Sudeep Choudhary, Jharia (IN); Raghav Bali, Delhi (IN); Anurag Das, Bangalore (IN); Subhadip Maji, Medinipur (IN)

(73) Assignee: Optum, Inc., Minnetonka, MN (US)

( * ) Notice: Subject to any disclaimer, the term of this patent is extended or adjusted under 35 U.S.C. 154(b) by 0 days.

(21) Appl. No.: 17/405,583

(22) Filed: Aug. 18, 2021

(65) Prior Publication Data

US 2023/0059399 A1 Feb. 23, 2023

(51) Int. Cl.
*G06T 19/00* (2011.01)
*G06F 3/01* (2006.01)
*G06V 40/20* (2022.01)
*G06F 18/22* (2023.01)
*G06F 18/2413* (2023.01)
*A61B 5/16* (2006.01)
*G06N 20/00* (2019.01)

(52) U.S. Cl.
CPC ............ *G06T 19/006* (2013.01); *G06F 3/011* (2013.01); *G06F 3/017* (2013.01); *G06F 18/22* (2023.01); *G06F 18/24137* (2023.01); *G06V 40/28* (2022.01); *A61B 5/165* (2013.01); *G06N 20/00* (2019.01)

(58) Field of Classification Search
CPC ........ G06T 19/006; G06F 3/011; G06F 3/017; G06K 9/6215; G06K 9/6272; G06V 40/28; A61B 5/165; G06N 20/00
See application file for complete search history.

(56) References Cited

U.S. PATENT DOCUMENTS

| | | | |
|---|---|---|---|
| 9,030,495 B2 * | 5/2015 | McCulloch | G09G 5/377 |
| | | | 715/708 |
| 9,131,053 B1 | 9/2015 | Tan et al. | |
| 9,308,445 B1 | 4/2016 | Merzenich et al. | |
| 10,482,333 B1 * | 11/2019 | el Kaliouby | G16H 20/70 |
| 10,524,715 B2 * | 1/2020 | Sahin | A61B 5/165 |
| 10,559,221 B2 | 2/2020 | Martucci et al. | |
| 10,839,201 B2 | 11/2020 | Johnson et al. | |

(Continued)

OTHER PUBLICATIONS

Sahin NT, Keshav NU, Salisbury JP, Vahabzadeh A. Safety and Lack of Negative Effects of Wearable Augmented-Reality Social Communication Aid for Children and Adults with Autism. Journal of Clinical Medicine. 2018; 7(8):188. (Year: 2018).*

(Continued)

*Primary Examiner* — Motilewa Good-Johnson
(74) *Attorney, Agent, or Firm* — Alston & Bird LLP

(57) ABSTRACT

Various embodiments of the present invention provide methods, apparatus, systems, computing devices, computing entities, and/or the like for performing augmented reality assistance mode functionalities. Certain embodiments utilize systems, methods, and computer program products that perform augmented reality assistance mode functionalities by using at least one of environment familiarity predictions, assistance mode triggering need determinations, and threat detection machine learning models.

18 Claims, 9 Drawing Sheets

(56) References Cited

U.S. PATENT DOCUMENTS

| | | | |
|---|---|---|---|
| 2012/0330869 A1* | 12/2012 | Durham | G06N 5/022 706/16 |
| 2013/0293586 A1* | 11/2013 | Kaino | G06F 3/005 345/633 |
| 2017/0238860 A1* | 8/2017 | el Kaliouby | A61B 5/7267 |
| 2017/0319123 A1* | 11/2017 | Voss | G16H 40/63 |
| 2017/0365101 A1* | 12/2017 | Samec | G02B 27/017 |
| 2018/0303397 A1* | 10/2018 | Krupat | A61B 5/4842 |
| 2019/0172458 A1* | 6/2019 | Mishra | G06K 9/6262 |
| 2019/0333629 A1 | 10/2019 | Torres | |
| 2020/0037943 A1 | 2/2020 | Chaja et al. | |
| 2020/0211292 A1* | 7/2020 | Wu | G06F 30/12 |
| 2020/0268298 A1 | 8/2020 | Wall | |
| 2020/0337631 A1 | 10/2020 | Sahin | |
| 2020/0405257 A1 | 12/2020 | Samec et al. | |
| 2021/0022657 A1 | 1/2021 | Voss et al. | |
| 2021/0133509 A1* | 5/2021 | Wall | G16H 10/20 |
| 2022/0057519 A1* | 2/2022 | Goldstein | G01S 17/04 |
| 2022/0067376 A1* | 3/2022 | Lee | G06K 9/0053 |

OTHER PUBLICATIONS

"Autism Fact Sheet," National Autism Association, (2 pages), (article, online), [Retrieved from the Internet Nov. 15, 2021] <URL: https://nationalautismassociation.org/resources/autism-fact-sheet/?gclid=Cj0KCQjwvvj5BRDkARIsAGD9vIKF3q_vDVBPDpE3ZgO405UL9cbhwsfYlkvvDdbKvfsSXgUE0um1QI4aAoeuEALw_wcB>.

"Autism's Cost," Beacon Health Options, (2 pages), (article, online), [Retrieved from the Internet Nov. 15, 2021] <URL: https://www.beaconhealthoptions.com/autisms-cost/>.

"Data & Statistics on Autism Spectrum Disorder," Center for Disease Control and Prevention, (2 pages), Sep. 25, 2020, (article, online), [Retrieved from the Internet Nov. 15, 2021] <URL: https://www.cdc.gov/ncbddd/autism/data.html>.

Anwar, Suzan et al. "Real Time Face Expression Recognition of Children With Autism," International Academy of Engineering and Medical Research, vol. 1, Issue 1, Oct.-Nov. 2016, pp. 1-7.

Barry, Amy. "7 of the Best Apps For Children With Autism|Autism Awareness Month 2020," Bridging Apps, Apr. 15, 2020, (article, online), (9 pages), [Retrieved from the Internet Nov. 15, 2021] <URL: https://web.archive.org/web/20201206003901/https//www.bridgingapps.org/2020/04/7-best-apps-children-autism/>.

Casas, Xavier et al. "A Kinect-Based Augmented Reality System For Individuals With Autism Spectrum Disorders," In Proceedings of the International Conference on Computer Graphics Theory and Applications, (GRAPP—2012), Feb. 24, 2012, pp. 440-446, DOI: 10.5220/0003844204400446, ISBN: 978-989-8565-02-0 . . . .

Deweerdt, Sarah. "People With Autism Sometimes Give Ambiguous Looks," Spectrum, (3 pages), Jan. 2, 2019, (article, online), [Retrieved from the Internet Nov. 15, 2021] <URL: https://www.spectrumnews.org/news/people-autism-sometimes-give-ambiguous-looks/>.

Lee, B.K. et al. "Increased Risk of Injury and Accident In Children With Autism," Center For Autism and Developmental Disabilities Epidemiology (CADDE), Johns Hopkins Bloomberg School of Public Health, (1 page), (article, online), [Retrieved from the Internet Nov. 15, 2021] <URL: https://www.jhsph.edu/research/centers-and-institutes/wendy-klag-center-for-autism-and-developmental-disabilities/_documents/presentations/IMFAR06_Injury.pdf>.

Liu, Runpeng et al. "Feasibility Of An Autism-Focused Augmented Reality Smartglasses System For Social Communication and Behavioral Coaching," Frontiers In Pediatrics, vol. 5, Article 145, pp. 1-8, Jun. 26, 2017, DOI: 10.3389/fped.2017.00145.

Mayo Clinic Staff. "Autism Spectrum Disorder—Systems and Causes," Mayo Clinic, Mayo Clinic, (5 pages), (article, online), [Retrieved from the Internet] <URL: https://www.mayoclinic.org/diseases-conditions/autism-spectrum-disorder/symptoms-causes/syc-20352928?utm_source=Google&utm_medium=abstract&utm_content=Autism&utm_campaign=Knowledge-panel>.

Sampol, Celia. "An Augmented Reality App To Help Children With Autism," MedicalExpo e-Magazine, Jun. 23, 2020, (5 pages), (article, online), [Retrieved from the Internet Nov. 15, 2021] <URL: https://emag.medicalexpo.com/an-augmented-reality-app-to-help-children-with-autism/>.

* cited by examiner

DYNAMIC TRIGGERING OF AUGMENTED REALITY ASSISTANCE MODE FUNCTIONALITIES

BACKGROUND

Various embodiments of the present invention address technical challenges related to augmented reality assistance mode functionalities. Various embodiments of the present invention disclose innovative techniques for performing augmented reality assistance mode functionalities.

BRIEF SUMMARY

In general, embodiments of the present invention provide methods, apparatus, systems, computing devices, computing entities, and/or the like for performing augmented reality assistance mode functionalities. Certain embodiments utilize systems, methods, and computer program products that perform augmented reality assistance mode functionalities by using at least one of environment familiarity predictions, assistance mode triggering need determinations, and threat detection machine learning models.

In accordance with one aspect, a method is provided. In one embodiment, the method comprises generating, based at least in part on current location data associated with a current end-user physical environment of the augmented reality device and a real-time video stream of the current end-user physical environment of the augmented reality device, an environment familiarity prediction for the current end-user physical environment; generating, based at least in part on the environment familiarity prediction, an assistance mode triggering need determination for the augmented reality assistance mode functionalities; in response to determining that the assistance mode triggering need determination is an affirmative assistance mode triggering need determination: determining, based at least in part on the real-time video stream (and, in some embodiments, additionally global positioning system (GPS) data, gyroscope data, accelerometer data, heart rate sensor data, blood pressure sensor data, and/or the like) and by utilizing a threat detection machine learning model, one or more detected threat indications for the current end-user physical environment; and providing the one or more detected threat indications to the augmented reality device to present using one or more augmented reality visualizations.

In accordance with another aspect, a computer program product is provided. The computer program product may comprise at least one computer-readable storage medium having computer-readable program code portions stored therein, the computer-readable program code portions comprising executable portions configured to generate, based at least in part on current location data associated with a current end-user physical environment of the augmented reality device and a real-time video stream (and, in some embodiments, additionally global positioning system (GPS) data, gyroscope data, accelerometer data, heart rate sensor data, blood pressure sensor data, and/or the like) of the current end-user physical environment of the augmented reality device, an environment familiarity prediction for the current end-user physical environment; generate, based at least in part on the environment familiarity prediction, an assistance mode triggering need determination for the augmented reality assistance mode functionalities; in response to determining that the assistance mode triggering need determination is an affirmative assistance mode triggering need determination: determine, based at least in part on the real-time video stream (and, in some embodiments, additionally global positioning system (GPS) data, gyroscope data, accelerometer data, heart rate sensor data, blood pressure sensor data, and/or the like) and by utilizing a threat detection machine learning model, one or more detected threat indications for the current end-user physical environment; and provide the one or more detected threat indications to the augmented reality device to present using one or more augmented reality visualizations.

In accordance with yet another aspect, an apparatus comprising at least one processor and at least one memory including computer program code is provided. In one embodiment, the at least one memory and the computer program code may be configured to, with the processor, cause the apparatus to generate, based at least in part on current location data associated with a current end-user physical environment of the augmented reality device and a real-time video stream (and, in some embodiments, additionally global positioning system (GPS) data, gyroscope data, accelerometer data, heart rate sensor data, blood pressure sensor data, and/or the like) of the current end-user physical environment of the augmented reality device, an environment familiarity prediction for the current end-user physical environment; generate, based at least in part on the environment familiarity prediction, an assistance mode triggering need determination for the augmented reality assistance mode functionalities; in response to determining that the assistance mode triggering need determination is an affirmative assistance mode triggering need determination: determine, based at least in part on the real-time video stream (and, in some embodiments, additionally global positioning system (GPS) data, gyroscope data, accelerometer data, heart rate sensor data, blood pressure sensor data, and/or the like) and by utilizing a threat detection machine learning model, one or more detected threat indications for the current end-user physical environment; and provide the one or more detected threat indications to the augmented reality device to present using one or more augmented reality visualizations.

In general, any predictive inferences that are discussed herein as being performed based at least in part on a real-time video stream can be performed based at least in part on at least one of a real-time video stream, global positioning system (GPS) data, gyroscope data, accelerometer data, heart rate sensor data, blood pressure sensor data, and the like.

BRIEF DESCRIPTION OF THE DRAWINGS

Figure 1:
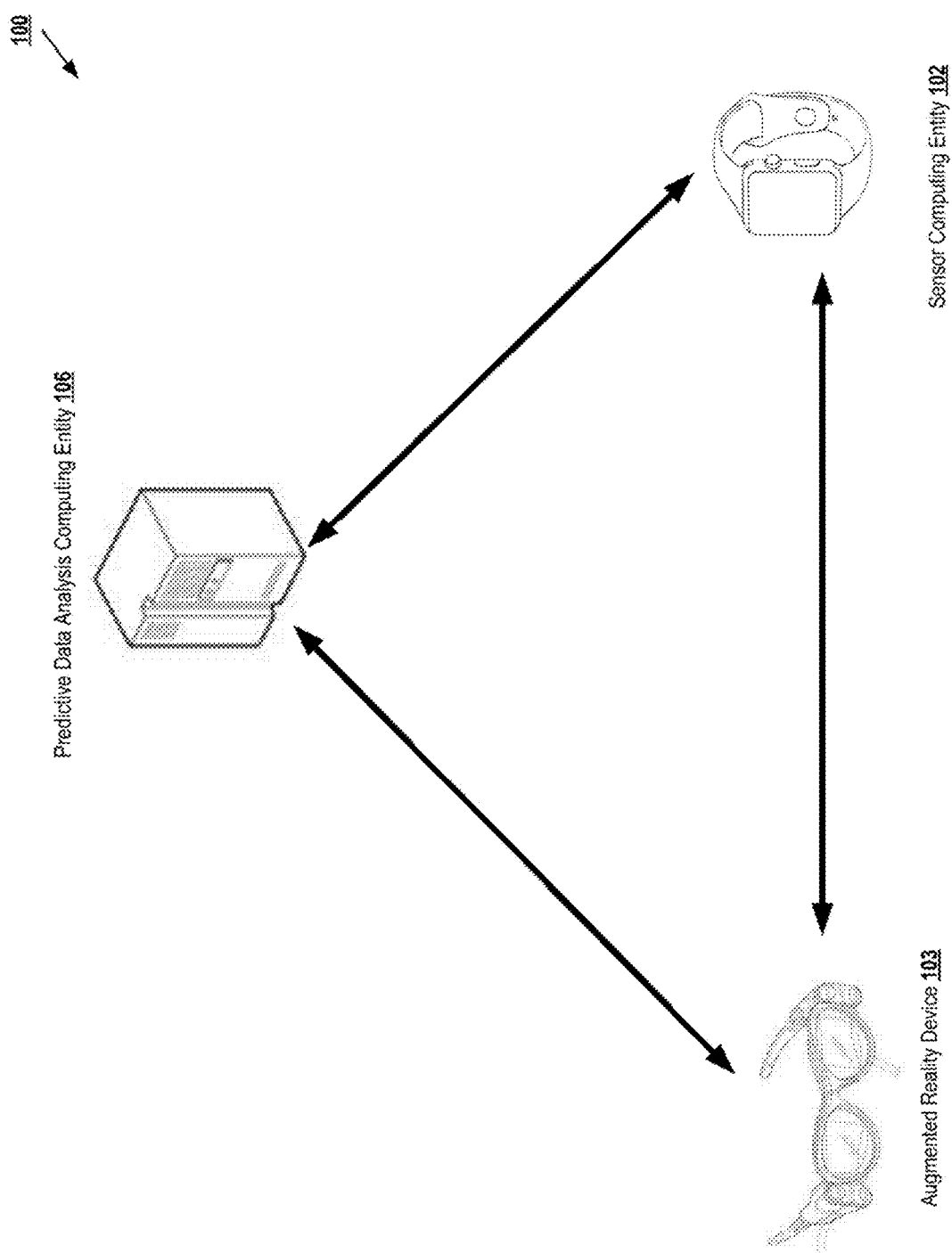

Having thus described the invention in general terms, reference will now be made to the accompanying drawings, which are not necessarily drawn to scale, and wherein:

FIG. 1 provides an exemplary overview of a hardware architecture that can be used to practice embodiments of the present invention.

Figure 2:
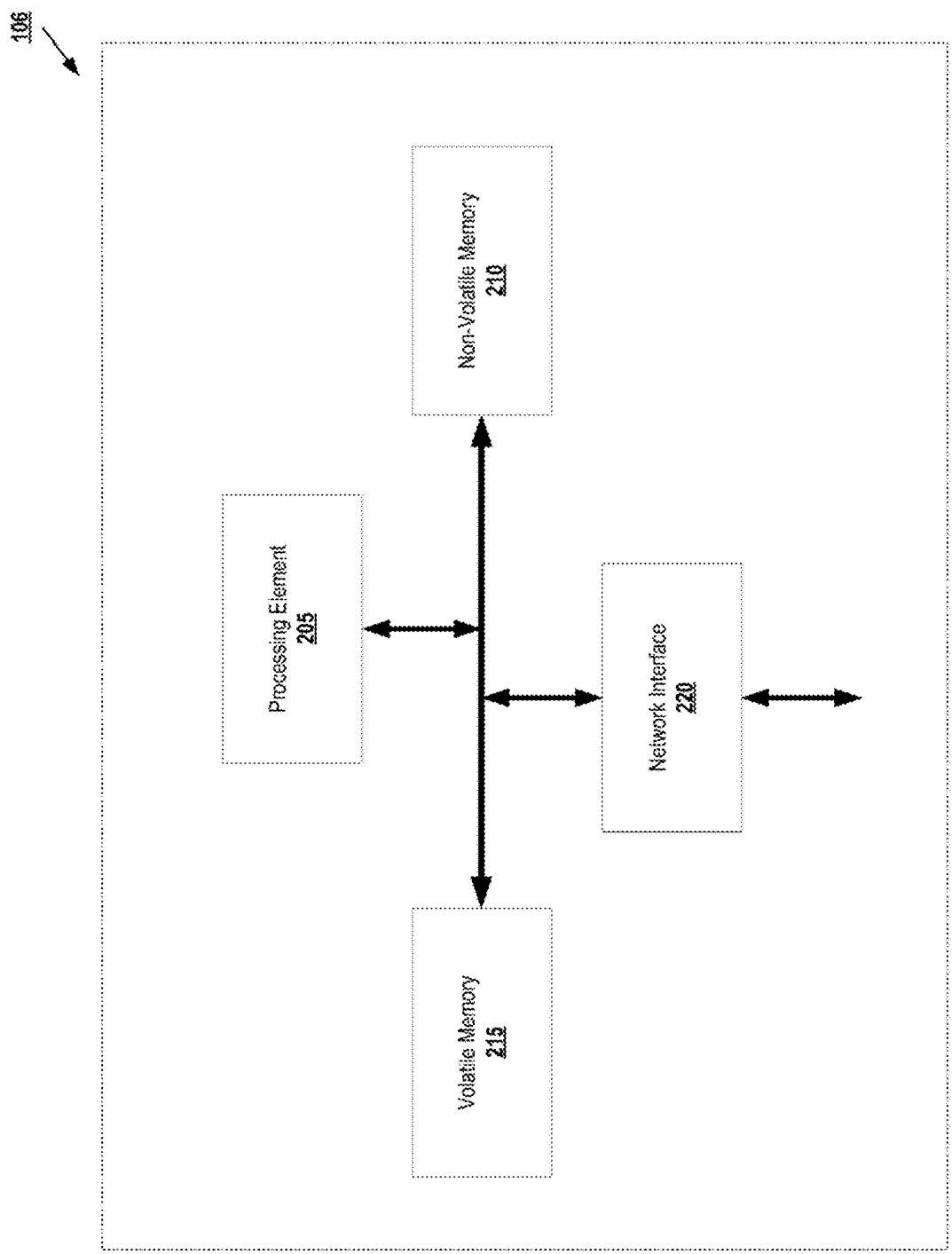

FIG. 2 provides an example predictive data analysis computing entity, in accordance with some embodiments discussed herein.

Figure 3:
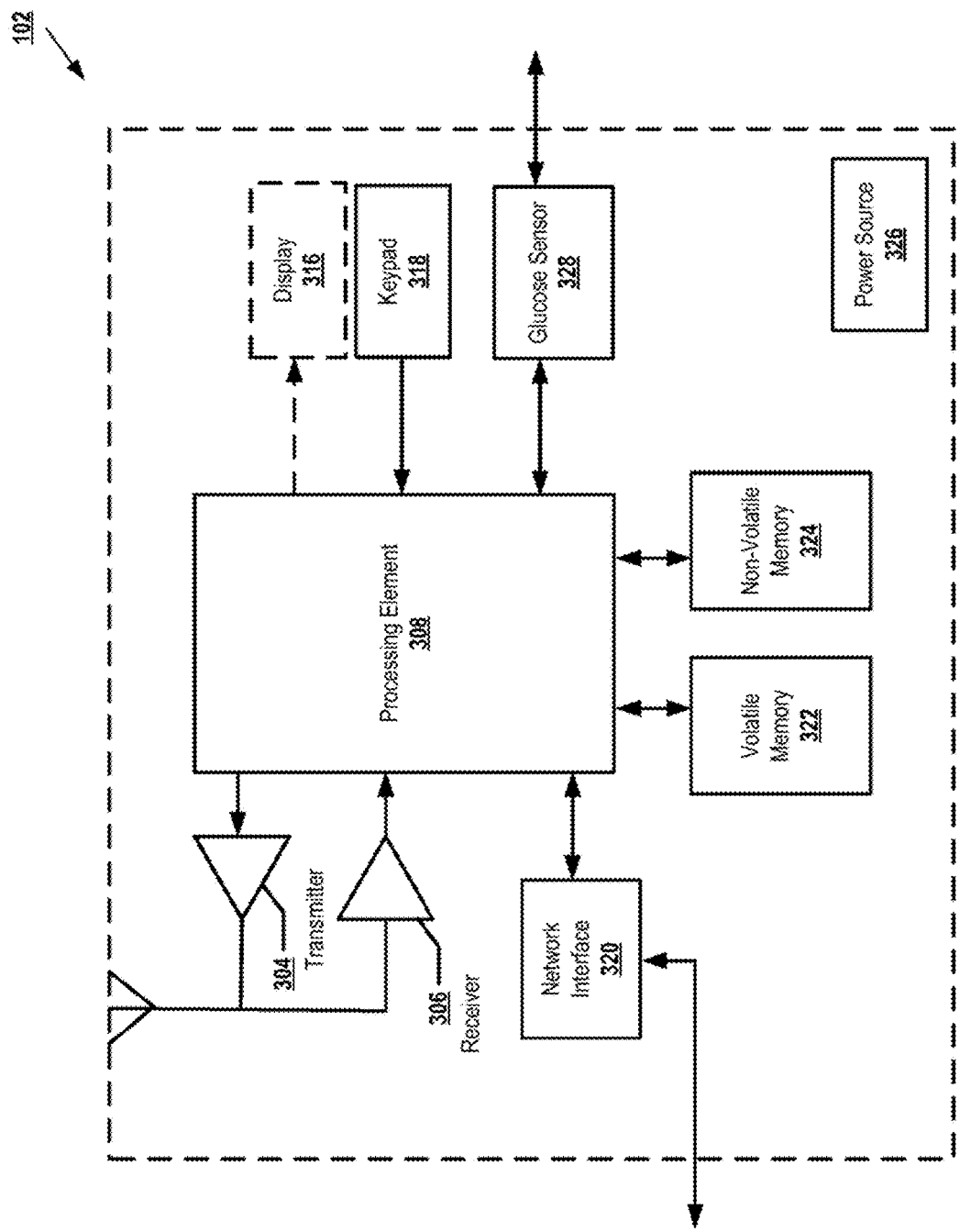

FIG. 3 provides an example sensor computing entity, in accordance with some embodiments discussed herein.

Figure 4:
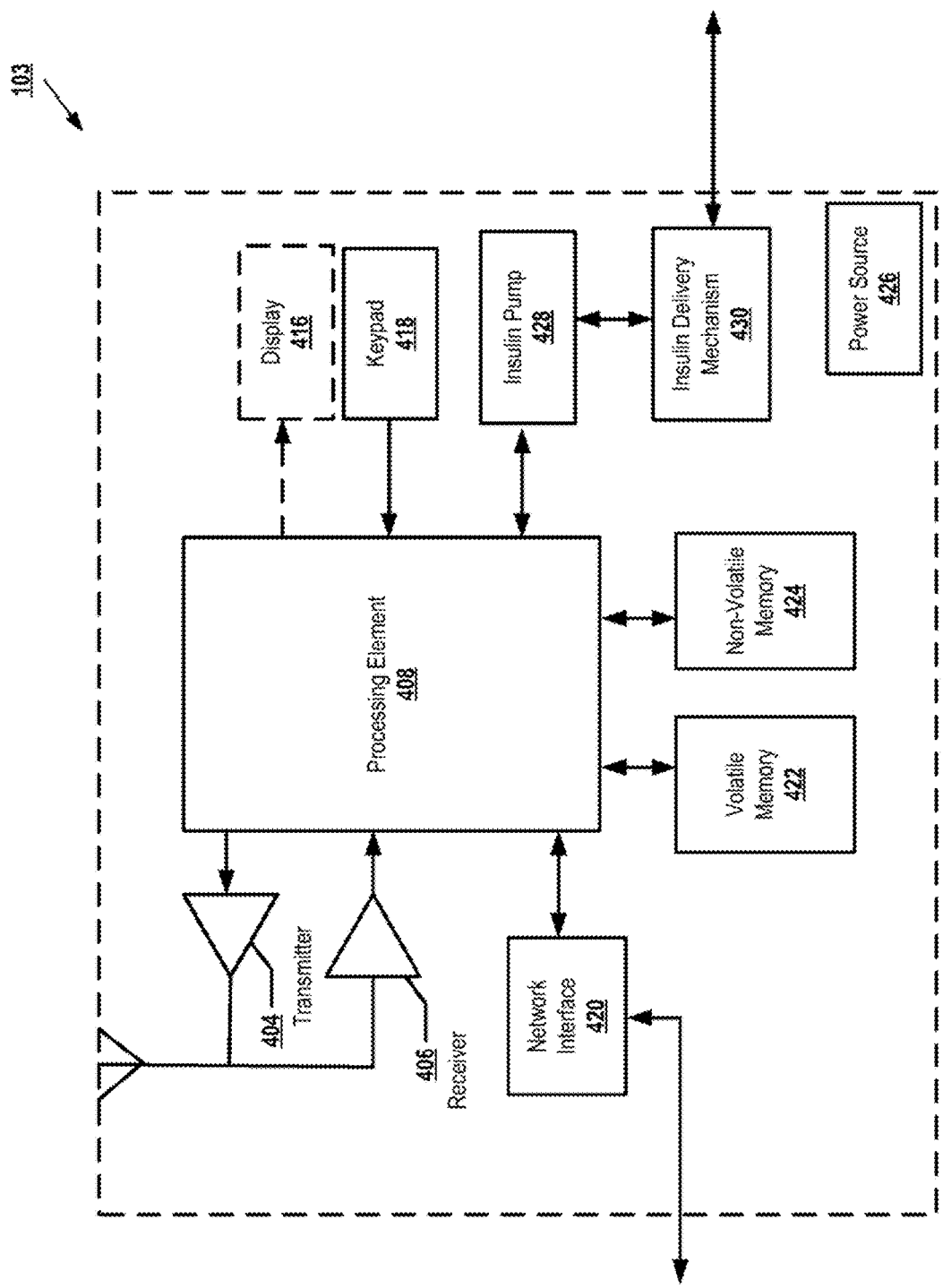

FIG. 4 provides an example augmented reality device, in accordance with some embodiments discussed herein.

Figure 5:
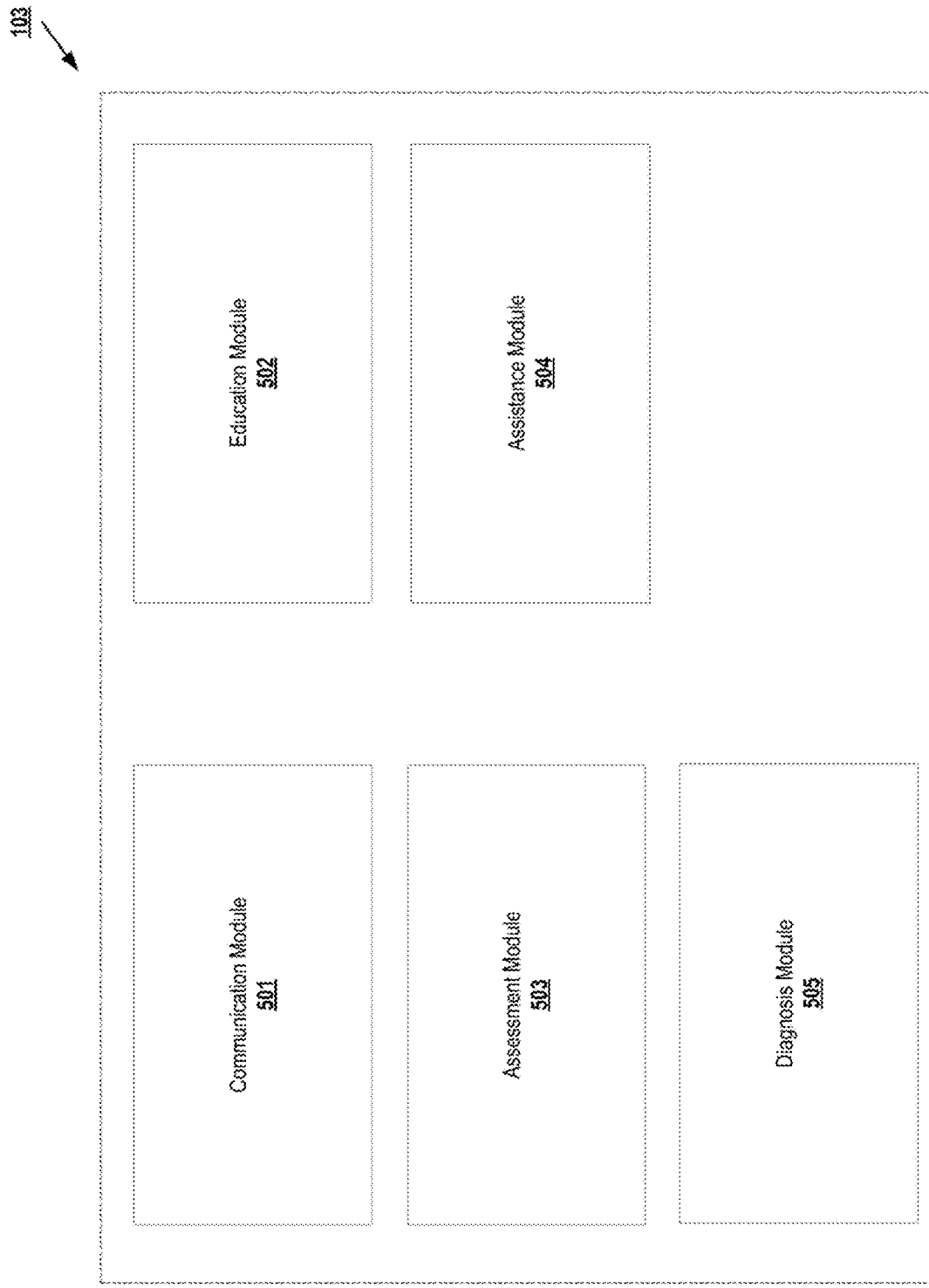

FIG. 5 provides a block diagram of the software architecture of the augmented reality device, in accordance with some embodiments discussed herein.

Figure 6:

FIG. 6 provides an operational example of an emotional awareness guideline, in accordance with some embodiments discussed herein.

Figure 7:
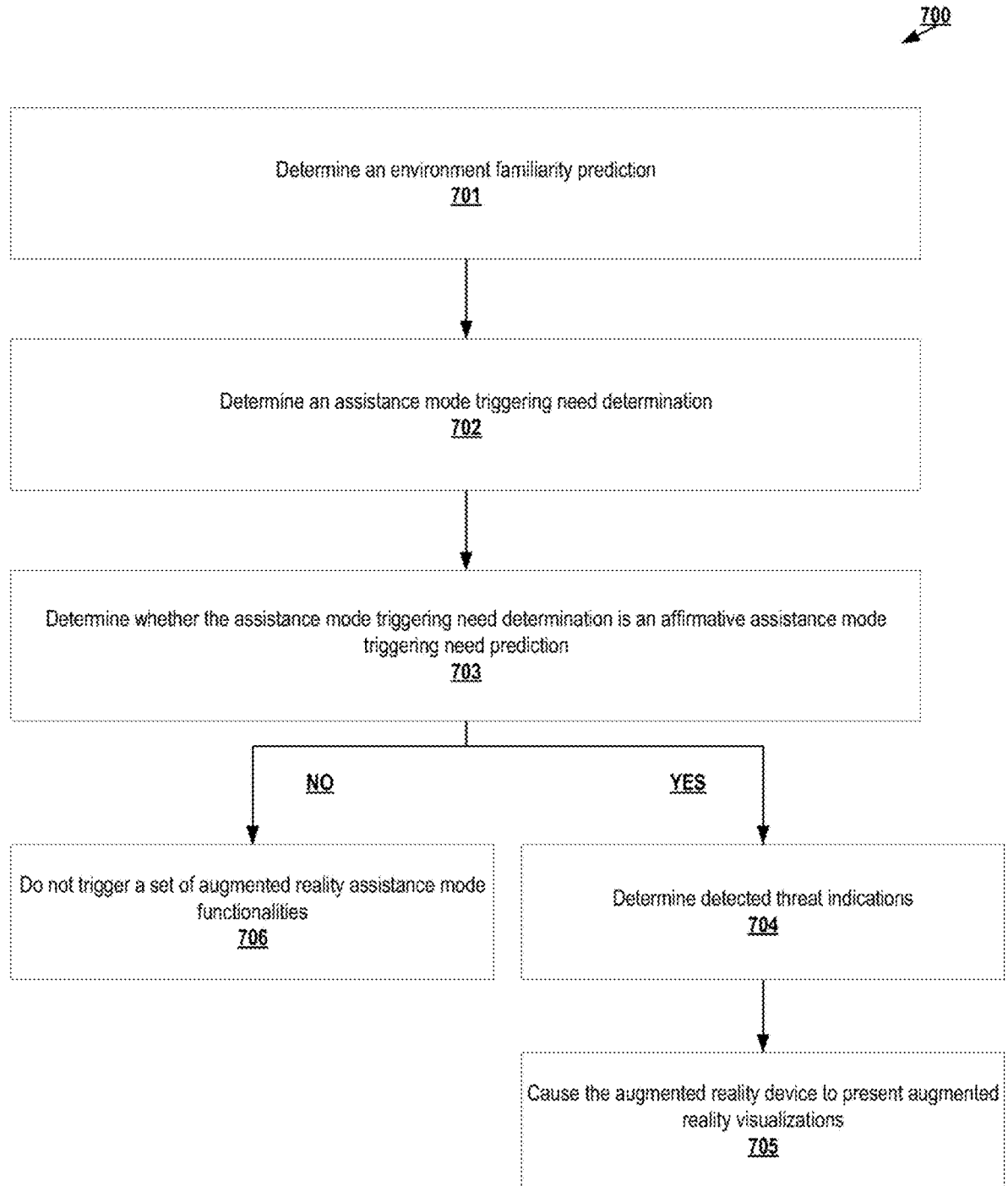

FIG. 7 is a flowchart of an example process for performing a set of augmented reality assistance mode functionalities using an automatic triggering mechanism, in accordance with some embodiments discussed herein.

Figure 8:
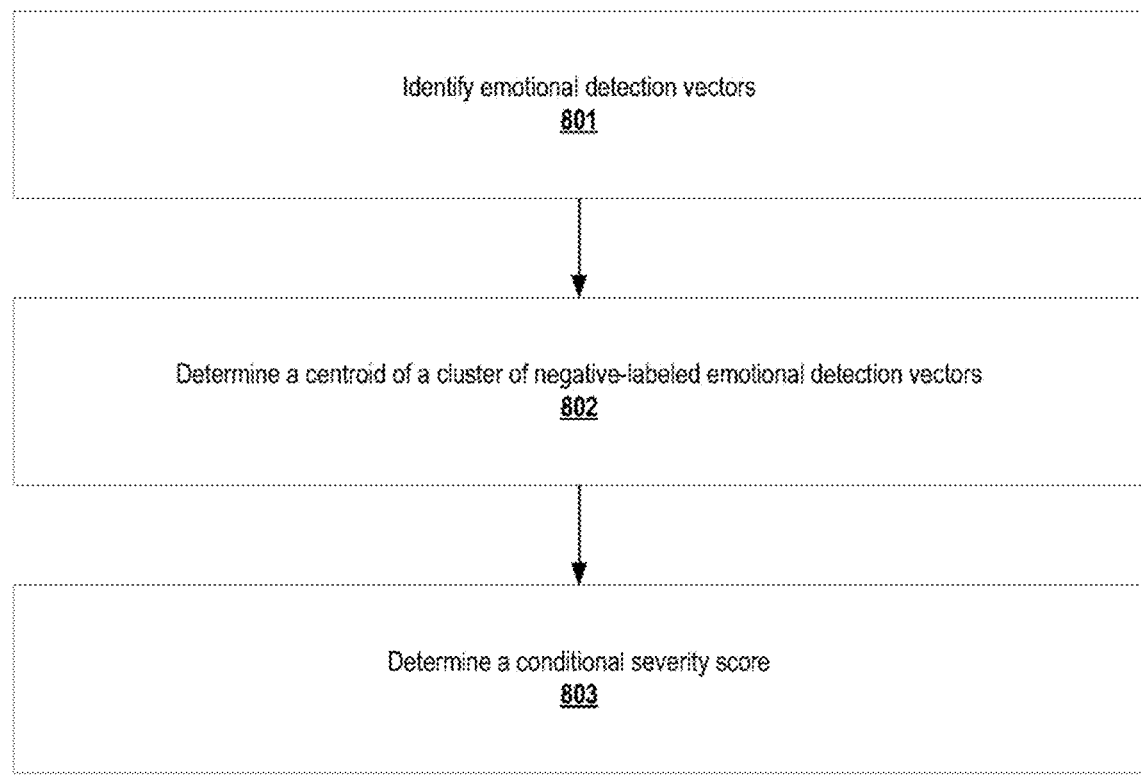

FIG. 8 is a flowchart of an example process for generating a conditional severity measure, in accordance with some embodiments discussed herein.

Figure 9:
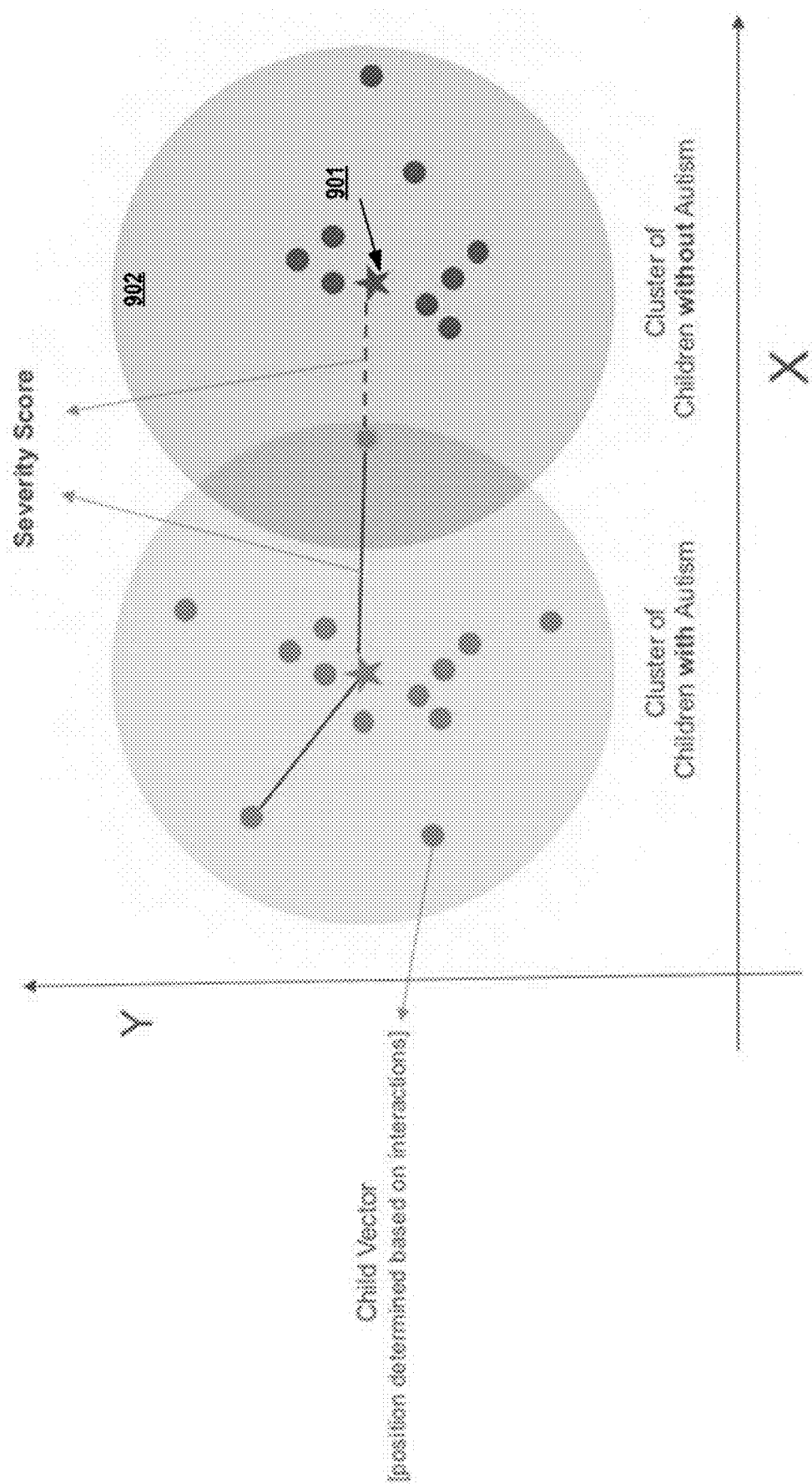

FIG. 9 provides an operational example of generating a distance measure between an emotional detection vector to a centroid of a cluster of negative-labeled emotional detection vectors, in accordance with some embodiments discussed herein.

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, one of ordinary skill in the art will recognize that the disclosed concepts can be used to perform other types of data analysis.

1I. Overview and Technical Advantages

Various embodiments of the present invention provide techniques for providing augmented reality assistance mode functionalities in a dynamically triggerable manner. The noted techniques improve the efficiency of augmented reality devices by removing the computationally expensive augmented reality assistance mode functionalities from a default operational mode of the augmented reality devices, while nevertheless minimizing the utility tradeoff resulting from this removal by ensuring that the augmented reality assistance mode functionalities can be enabled using automatic triggers. In doing so, various embodiments of the present invention increase the computational efficiency of augmented reality devices, reduce the number of computationally expensive operations performed on the noted devices, and make substantial technical contributions to the field of augmented reality computing.

In some embodiments, an "augmented reality device" includes an electronic device comprising at least one processor and memory that augments real world elements as presented to the user. Examples of an augmented reality device include augmented reality glasses, augmented reality headsets, and mobile devices including an augmented reality application. Examples of augmented reality devices further include mixed reality devices and virtual reality devices.

An exemplary application of various embodiments of the present invention relates to assisting end users of augmented reality devices that suffer from autism. Autism or Autism Spectrum Disorder (ASD) is the fastest growing developmental disorder that impairs the ability to communicate and interact. As it affects the nervous system, people suffering with autism might experience difficulties in various aspects. Aspects of the various embodiments of the present invention propose an artificial intelligence (AI) and augmented reality (AR) based solution that can help in treating ASD. This solution can be deployed as a smartphone application, a Google Glass type wearable device, a plugin for video conferencing solutions, or even a web-browser based application.

In some embodiments, a proposed device has five primary modes of operation: a communication mode, an education mode, an assessment mode, a diagnosis mode, and an assistance mode. The noted modes are described below. Communication mode is the default mode of the device. The device starts working as soon as somebody comes in contact with the person using the device. Communication mode has multiple AI and AR powered features that are configured to make the communication easier for the person with ASD. Some of these features are as follows: augmented real-time emotion awareness (e.g., with emojis/text); augmented speech transcriptions (e.g., with images/emojis); sign language understanding (e.g., with augmented images/text); generating prompts for communicating back (e.g., with prompts like: say 'Hello', or say 'Good Morning'); and raising awareness of the user surroundings. In an education mode, the solution will focus on educating the user in different ways. Some of the features of education mode may be as follows: speech command training, emotion training, and direction Training. In an assessment mode, the solution assesses the person with ASD to provide feedback on progress. Assessment mode may enable the following features: assessing speech command responses, emotion detection game/quiz scores, and assessing eye contact with respect to augmented eye targets. Diagnosis mode is primarily for care-takers, such as for doctors or family-members. This solution collects information related to the user's behavior and progress when it is operated in the previously-discussed model. While assisting the user with interactions, the solution tracks how the patient is responding to different commands, signals, signs, etc. This kind of feedback can help the care-takers in understanding the patient's condition (improvement areas, challenges, etc.). The assistance mode can help the person wearing the device to be aware of any potential fall or collision scenarios. The user would be warned of any fast approaching vehicles or any other obstacles. Likewise, depth estimation could warn the user in case there is shallow ground/higher surface while walking. In some embodiments, the communication mode is the default mode of the solution. In some embodiments, the education mode, assessment mode, and diagnostic mode need to be triggered manually. Assistance mode, on the other hand, works with an automatic switching mechanism that triggers automatically based at least in part on a user's activity. FIG. 7 shows the overall architecture of the automatic switching mechanism for the assistance mode. With this mechanism, the assistance mode can be triggered automatically and become part of the communication mode.

II. Definitions

The term "environment familiarity prediction" may refer to a data entity that is configured to describe an inferred prediction about whether a current end-user physical environment of an end user of an augmented reality device is deemed to be a familiar environment for the end user. In some embodiments, an affirmative environment familiarity prediction describes that a corresponding current end-user physical environment is deemed to be a familiar environment, while a negative environment familiarity prediction describes that a corresponding current end-user physical environment is deemed an unfamiliar physical environment. In some embodiments, the environment familiarity prediction is determined as an affirmative environment familiarity prediction if a determined location of the current end-user physical environment of the end user is deemed to be a familiar location (e.g., a location that is designated as a home location may be deemed to be a familiar location and thus, if a determined location of a current end-user physical environment of an end user is deemed to be the home location, then the current end-user physical environment may be associated with an affirmative environment familiarity prediction). In some embodiments, the environment familiarity prediction is determined as an affirmative environment familiarity prediction if at least n (e.g., at least one) detected participants in the current end-user physical environment of the end user are deemed to be familiar participants (e.g., a participant that is designated as an immediate family member may be deemed to be a familiar participant and thus, if at least n determined participants of a current end-user physical environment of an end user are deemed to be familiar participants, then the current end-user physical environment may be associated with an affirmative environment familiarity prediction). In some embodiments, the environment familiarity prediction is determined as an affirmative environment familiarity prediction if at least one of the following three conditions is satisfied: (i) if a determined location of the current end-user physical environment of the end user is deemed to be a familiar location, (ii) if one or more detected participants in the current end-user physical environment of the end user are deemed to be familiar participants, and (iii) if the vital parameters (e.g., blood pressure, heart rate, orientation, and/or the like) of the end-user are within normal ranges. In some embodiments, the environment familiarity prediction is determined as an affirmative environment familiarity prediction if at least one of the following two conditions satisfied: (i) if a determined location of the current end-user physical environment of the end user is deemed to be a familiar location, and (ii) if at least n detected participants in the current end-user physical environment of the end user are deemed to be familiar participants. In some embodiments, the environment familiarity prediction for a current end-user physical environment of an end user is determined based at least in part on at least one of the following: (i) data describing designated location regions that are deemed to be familiar location regions for the end user, (ii) data describing designated participant profiles that are deemed to be familiar participants for the end user, and (iii) data describing normal ranges for vital parameters of an end-user.

The term "assistance mode triggering determination" may refer to a data entity that is configured to describe whether one or more augmented reality assistance mode functionalities of an augmented reality device should be automatically triggered. In some embodiments, an augmented reality device is associated with a set of augmented reality assistance mode functionalities that are configured to provide instructions to an end user profile of the augmented reality device about navigating the physical, sensory, and/or social challenges associated with a current end-user physical environment of the end user profile. In some of the noted embodiments, the aforementioned set of augmented reality assistance mode functionalities of the augmented reality device are automatically triggered upon satisfaction of at least one of a set of triggering conditions, where each triggering condition in the set of triggering conditions may be associated with one or more statically-defined triggering criteria and/or one or more dynamically-defined triggering criteria. For example, in some embodiments, the triggering conditions for a set of augmented reality assistance mode functionalities may include (e.g., may consist of) a dynamically-defined triggering criterion that is satisfied whenever a current end-user physical environment of an end user profile of an augmented reality device is associated with an affirmative environment familiarity prediction. In some embodiments, the assistance mode triggering determination for a set of augmented reality assistance mode functionalities is deemed to be an affirmative assistance mode triggering determination if the assistance mode triggering determination describes that the set of augmented reality assistance mode functionalities should be automatically triggered, while the assistance mode triggering determination for a set of augmented reality assistance mode functionalities is deemed to be a negative assistance mode triggering determination if the assistance mode triggering determination describes that the set of augmented reality assistance mode functionalities should not be automatically triggered. In some embodiments, the assistance mode triggering determination for a set of augmented reality assistance mode functionalities is set to an affirmative assistance mode triggering determination if a current end-user physical environment of an end user profile of a corresponding augmented reality device is associated with an affirmative environment familiarity prediction. In some embodiments, the assistance mode triggering determination for a set of augmented reality assistance mode functionalities is set to an affirmative assistance mode triggering determination if both of the following triggering criteria are satisfied: (i) a current end-user physical environment of an end user profile of a corresponding augmented reality device is associated with an affirmative environment familiarity prediction, and (ii) one or more other triggering criteria are satisfied. In some embodiments, the assistance mode triggering determination for a set of augmented reality assistance mode functionalities is set to an affirmative assistance mode triggering determination if either of the following triggering conditions is satisfied: (i) a current end-user physical environment of an end user profile of a corresponding augmented reality device is associated with an affirmative environment familiarity prediction, and (ii) one or more other triggering conditions are satisfied.

The term "augmented reality assistance mode functionality" may refer to a data entity that is configured to describe a set of computer-implemented operations that are configured to cause an augmented reality device to provide instructions to an end user of the augmented reality device. For example, an augmented reality assistance mode functionality may describe a set of computer-implemented operations that are configured to cause an augmented reality device to present one or more augmented reality visualizations (e.g., one or more augmented reality notifications) corresponding one or more detected threats in a current end-user physical environment of the end user. For example, in some embodiments, a set of augmented reality assistance mode functionalities may be configured to, in response to determining that the assistance mode triggering need determination is an affirmative assistance mode triggering need determination, perform the following two operations: (i) determine, based at least in part on a real-time video stream and by utilizing a threat detection machine learning model, one or more detected threat indications for a current end-user physical environment of an end user profile of an augmented reality device, and (ii) cause the augmented reality device (e.g., by providing threat detection data to the augmented reality device) to present one or more augmented reality visualizations corresponding to the one or more detected threat indications. In some embodiments, a set of augmented reality assistance mode functionalities may be configured to provide assistance to an end user of an augmented reality device to be aware of any potential fall scenarios and/or any potential collision scenarios in a current end-user physical environment of the corresponding end user. In some embodiments, a set of augmented reality assistance mode functionalities may be configured to provide assistance to an end user of an augmented reality device about fast approaching vehicles or other obstacles. In some embodiments, a set of augmented reality assistance mode functionalities may be configured to provide assistance to an end user of an augmented reality device about shallow grounds and/or higher surfaces in the pathway of the end user. In some embodiments, a set of augmented reality assistance mode functionalities may be triggered automatically, manually, or both in manners. For example, in some embodiments, a set of augmented reality assistance mode functionalities may be triggered in response to determining that the assistance mode triggering need determination is an affirmative assistance mode triggering need determination. As another example, in some embodiments, a set of augmented reality assistance mode functionalities may be triggered either manually or dynamically in response to determining that the assistance mode triggering need determination is an affirmative assistance mode triggering need determination. In some embodiments, the detected threat indications described by augmented reality visualizations that are generated as a result of performing a set of augmented reality assistance mode functionalities may be determined based at least in part on a location map of the current end-user physical environment of the end user. In some embodiments, the detected threat indications described by augmented reality visualizations that are generated as a result of performing a set of augmented reality assistance mode functionalities may be determined based at least in part on a real-time video stream of the current end-user physical environment of the augmented reality device.

The term "location-wise familiarity prediction" may refer to a data entity that is configured to describe an inferred prediction about whether a location designation of a current end-user physical environment of an end user of an augmented reality device is deemed to be a familiar location for the end user. In some embodiments, an affirmative location-wise familiarity prediction describes that a corresponding location designation of a current end-user physical environment is deemed to be a familiar location, while a negative location-wise familiarity prediction describes that a corresponding location designation of a current end-user physical environment is deemed to be an unfamiliar location. In some embodiments, the location-wise familiarity prediction for a current end-user physical environment is determined based at least in part on location data associated with the current physical environment, where the location data are configured to identify absolute coordinates and/or relative coordinates for a designated location of the current physical environment. Examples of location data include Global Positioning System (GPS) data. In some embodiments, a predicted environment familiarity prediction for a current end-user physical environment is determined based at least in part on a location-wise familiarity prediction and an interaction-wise familiarity prediction. In some embodiments, determining an environment familiarity prediction based a location-wise familiarity prediction and an interaction-wise familiarity prediction comprises: determining whether at least one of the location-wise familiarity prediction and the interaction-wise familiarity prediction describes an affirmative familiarity prediction; and in response to determining that the at least one of the location-wise familiarity prediction and the interaction-wise familiarity prediction describes the affirmative familiarity prediction, determining that the environment familiarity prediction is an affirmative environment familiarity prediction.

The term "interaction-wise familiarity prediction" may refer to a data entity that is configured to describe an inferred prediction about whether at least n detected participants in a current end-user physical environment of an end user of an augmented reality device are deemed to be familiar individuals to the end user. In some embodiments, an affirmative interaction-wise familiarity prediction describes that at least n detected participants of a current end-user physical environment are deemed to be familiar individuals, while a negative location-wise familiarity prediction describes that less than n detected participants of a current end-user physical environment are deemed to be familiar individuals. In some embodiments, the interaction-wise familiarity prediction for a current end-user physical environment is determined based at least in part on detected faces in the current physical environment, such as detected faces determined based at least in part on performing image/video analysis on a current video stream of the current physical environment. In some embodiments, determining an environment familiarity prediction based a location-wise familiarity prediction and an interaction-wise familiarity prediction comprises: determining whether at least one of the location-wise familiarity prediction and the interaction-wise familiarity prediction describes an affirmative familiarity prediction; and in response to determining that the at least one of the location-wise familiarity prediction and the interaction-wise familiarity prediction describes the affirmative familiarity prediction, determining that the environment familiarity prediction is an affirmative environment familiarity prediction.

The term "physiological condition severity prediction" may refer to a data entity that is configured to describe whether a determined physiological state of an end user of an augmented reality device is deemed to be a normal/regular physiological state. In some embodiments, the physiological condition severity prediction is an affirmative physiological condition severity prediction if the determined physiological state of the corresponding end user is deemed to be a normal/regular physiological state, while the physiological condition severity prediction is a negative physiological condition severity prediction if the determined physiological state of the corresponding end user is not deemed to be a normal/regular physiological state. In some embodiments, the physiological condition severity prediction for an end user is determined based at least in part on a current physiological data stream associated with the end-user profile, such as a current physiological stream that describes one or more biometric measurements and/or one or more physiological measurements associated with the end user (e.g., one or more heart rate measurements associated with the end user, one or more pulse rate measurements associated with the end user, one or more breathing rate measurements, one or more blood glucose level measurements, and/or the like). In some embodiments, the environment familiarity prediction for a current end-user physical environment of an end user of an augmented reality computing device is determined based at least in part on a physiological condition severity prediction for the end user. For example, in some embodiments, determining the assistance mode triggering need determination based at least in part on the physiological condition severity prediction and the environment familiarity prediction comprises: determining whether at least one of the physiological condition severity prediction and the environment familiarity prediction describes an affirmative determination; and in response to determining that the at least one of the physiological condition severity prediction and the environment familiarity prediction describes the affirmative determination, determining that the assistance mode triggering need determination is an affirmative assistance mode triggering need determination.

The term "threat detection machine learning model" may refer to a data entity that is configured to describe parameters, hyper-parameters, and/or defined operations of a model that is configured to process feature data associated with a current end-user physical environment of an end user in order to generate one or more threat detections for the current end-user physical environment. For example, the threat detection machine learning model may comprise an image/video processing component that is configured to process a real-time video stream of the current end-user physical environment of an end user in order to generate one or more threat detections for the current end-user physical environment. As another example, the threat detection machine learning model may comprise a component that is configured to process a map of the current end-user physical environment of an end user in order to generate one or more threat detections for the current end-user physical environment. In some embodiments, the inputs to the threat detection machine learning model include one or more time-stamped real-time video stream vectors. In some embodiments, the outputs of the threat detection machine learning model include one or more output vectors each describing a detected threat indication for a current end-user physical environment of the end user of an augmented reality device.

The term "interactive participant profile" may refer to a data entity that is configured to describe a detected individual with whom an end user associated with an end user profile of an augmented reality device is detected to be directly or indirectly interacting. In some embodiments, an interactive participant profile is determined based at least in part on face detections performed using a real-time video stream of the current end-user physical environment of the augmented reality device. In some embodiments, an interactive participant profile is determined based at least in part on data (e.g., calendar confirmation data, vehicle usage data, location tracking data, and/or the like) that describes participants of a particular event in a particular location that is associated with a current end-user physical environment of the augmented reality device. In some embodiments, a predictive data analysis computing entity may be configured to generate at least one of a predicted emotional state for an individual associated with an interactive participant profile and a predicted sign language translation for an individual associated with an interactive participant profile, as further described below.

The term "predicted emotional state" may refer to a data entity that is configured to describe an inferred emotional designation for a detected face of an individual associated with an interactive participant profile. In some embodiments, the predicted emotional state for an individual is determined (e.g., by a predictive data analysis computing entity that interacts with an augmented reality device) by first processing a real-time video stream of a current end-user physical environment of an end user using a face detection machine learning model (e.g., a convolutional neural network machine learning model) to detect a face associated with an interactive participant profile, and then processing the face using an emotion detection machine learning model (e.g., a supervised machine learning model that includes an image processing component) in order to generate the predicted emotional state of the individual associated with the interactive participant. In some of the noted embodiments, an emotion detection machine learning model is a trained machine learning model that is configured to process image/video data associated with a detected face of an individual in order to generate a predicted emotional state of the individual. Examples of inputs to an emotion detection machine learning model include a sequence of one or more image matrices (e.g., where each matrix value describes the color intensities of a pixel of a captured image), while outputs of an emotion detection machine learning model include a vector describing a predicted correlation value for each candidate emotional state of a set of candidate emotional states. In some embodiments, the predicted emotional state for an individual is determined (e.g., by a predictive data analysis computing entity that interacts with an augmented reality device) by first processing a real-time video stream of a current end-user physical environment of an end user using a face landmark detection machine learning model (e.g., a convolutional neural network machine learning model) to detect one or more facial landmarks of the individual, then processing the real-time video stream to detect one or more posture indications for the individual, and then processing the facial landmarks and the posture indications using an emotion detection machine learning model (e.g., a supervised machine learning model) in order to generate the predicted emotional state of the individual associated with the interactive participant. In some of the noted embodiments, an emotion detection machine learning model is a trained machine learning model that is configured to process data associated with detected facial features and posture indications of an individual in order to generate a predicted emotional state of the individual. Examples of inputs to an emotion detection machine learning model include a vector describing properties of each facial landmark and/or a vector describing properties of each posture indication, while outputs of an emotion detection machine learning model include a vector describing a predicted correlation value for each candidate emotional state of a set of candidate emotional states.

The term "predicted sign language translation" may refer to a data entity that is configured to describe inferred sign language interpretations for hand movements of an individual associated with an interactive participant profile. In some embodiments, a detected sign language translation is determined by processing a real-time video stream associated with a current end-user physical environment of an end user profile of an augmented reality device in order to detect one or more hand movements for the end user profile, and then processing the detected hand movements using a sign language detection machine learning model. In some of the noted embodiments, the sign language detection machine learning model is a supervised machine learning model that is configured to process hand movement detections associated with an interactive participant profile in order to generate the predicted sign language translation of the noted hand movement detections. In some embodiments, the inputs to the sign language detection machine learning model describe a sequence of vectors each describing a particular hand movement in a sequence, while the outputs of the sign language detection machine learning model include a text string describing text data associated with the predicted sign language translation.

The term "emotional detection vector" may refer to a data entity that is configured to describe a set of responses to a set of challenges (e.g., a set of emotional detection challenges, where each emotional detection challenge presents a face visualization and seeks a user detection of the emotional detection for the face visualization) for an individual. In some embodiments, when an emotional detection vector describes a set of responses by an individual deemed to have a target condition (e.g., autism), the emotional detection vector is deemed an affirmative-labeled emotional detection vector. In some embodiments, when an emotional detection vector describes a set of responses by an individual deemed not to have a target condition (e.g., autism), the emotional detection vector is deemed a negative-labeled emotional detection vector.

III. Computer Program Products, Methods, and Computing Entities

Embodiments of the present invention may be implemented in various ways, including as computer program products that comprise articles of manufacture. Such computer program products may comprise one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may comprise a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media comprise all computer-readable media (including volatile and non-volatile media).

In one embodiment, a non-volatile computer-readable storage medium may comprise a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also comprise a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also comprise read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also comprise conductive-bridging random access memory (CBRAM), phase-change random access memory (PRAM), ferroelectric random-access memory (FeRAM), non-volatile random-access memory (NVRAM), magneto-resistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may comprise random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SWIM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. Exemplary System Architecture

FIG. 1 is a schematic diagram of an example architecture 100 for an augmented reality framework. The architecture 100 comprises a predictive data analysis computing entity 106, an augmented reality device 103, and one or more sensor computing entities 102. The architecture 100 enables the augmented reality device 103 to provide one or more augmented reality functionalities to an end user of the augmented reality device, such as one or more augmented reality communication mode functionalities, one or more augmented reality education mode functionalities, one or more augmented reality assessment mode functionalities, one or more augmented reality assistance mode functionalities, and/or one or more augmented reality diagnosis mode functionalities.

In some embodiments, the computing entities depicted in FIG. 1 may communicate using one or more communication networks. Examples of communication networks comprise any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The predictive data analysis computing entity 106 may be configured to receive sensory data (e.g., physiological data streams, location data, and/or the like) from the one or more sensor computing entities 102, receive data (e.g., location data, video data, audio data, and/or the like) from the augmented reality device 103, process the received data to generate data configured to enable the augmented reality device 103 to perform one or more augmented reality functionalities (e.g., one or more augmented reality communication mode functionalities, one or more augmented reality education mode functionalities, one or more augmented reality assessment mode functionalities, one or more augmented reality assistance mode functionalities, and/or one or more augmented reality diagnosis mode functionalities) to an end user of the augmented reality device. Examples of sensory data provided to the predictive data analysis computing entity 106 include a current physiological stream that describes one or more biometric measurements and/or one or more physiological measurements associated with the end user (e.g., one or more heart rate measurements associated with the end user, one or more pulse rate measurements associated with the end user, one or more breathing rate measurements, one or more blood glucose level measurements, and/or the like). In some embodiments, at least some (e.g., all) of the functionalities discussed herein for the predictive data analysis computing entity 106 can be done by an edge computing entity.

Each computing entity that is depicted in FIG. 1 may include one or more storage subsystems. Each storage subsystem may comprise one or more storage units, such as multiple distributed storage units that are connected through a computer network. Each storage unit in the storage subsystem may store at least one of one or more information/data assets and/or one or more information/data about the computed properties of one or more information/data assets. Moreover, each storage unit in the storage subsystem may comprise one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Predictive Data Analysis Computing Entity

FIG. 2 provides a schematic of a predictive data analysis computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the predictive data analysis computing entity 106 may also comprise one or more network interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the predictive data analysis computing entity 106 may comprise or be in communication with one or more processing elements 205 (also referred to as processors, processing circuitry, and/or similar terms used herein interchangeably) that communicate with other elements within the predictive data analysis computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, another circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the predictive data analysis computing entity 106 may further comprise or be in communication with non-volatile media (also referred to as non-volatile storage, memory, memory storage, memory circuitry and/or similar terms used herein interchangeably). In one embodiment, the non-volatile storage or memory may comprise one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or information/data that is stored in a computer-readable storage medium using one or more database models, such as a hierarchical database model, network model, relational model, entity-relationship model, object model, document model, semantic model, graph model, and/or the like.

In one embodiment, the predictive data analysis computing entity 106 may further comprise or be in communication with volatile media (also referred to as volatile storage, memory, memory storage, memory circuitry and/or similar terms used herein interchangeably). In one embodiment, the volatile storage or memory may also comprise one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the predictive data analysis computing entity 106 with the assistance of the processing element 205 and operating system.

As indicated, in one embodiment, the predictive data analysis computing entity 106 may also comprise one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive data analysis computing entity 106 may be configured to communicate via wireless client communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the predictive data analysis computing entity 106 may comprise or be in communication with one or more input elements, such as a keyboard input, a mouse input, a touch screen/display input, motion input, movement input, audio input, pointing device input, joystick input, keypad input, and/or the like. The predictive data analysis computing entity 106 may also comprise or be in communication with one or more output elements (not shown), such as audio output, video output, screen/display output, motion output, movement output, and/or the like.

Exemplary Sensor Computing Entity

FIG. 3 provides an illustrative schematic representative of a sensor computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Sensor computing entities 102 can be operated by various parties. As shown in FIG. 3, the sensor computing entity 102 can comprise an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may comprise signaling information/data in accordance with air interface standards of applicable wireless systems. In this regard, the sensor computing entity 102 may be capable of operating with one or more air interface standards, communication protocols, modulation types, and access types. More particularly, the sensor computing entity 102 may operate in accordance with any of a number of wireless communication standards and protocols, such as those described above with regard to the predictive data analysis computing entity 106. In a particular embodiment, the sensor computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the sensor computing entity 102 may operate in accordance with multiple wired communication standards and protocols, such as those described above with regard to the predictive data analysis computing entity 106 via a network interface 320.

Via these communication standards and protocols, the sensor computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The sensor computing entity 102 can also download changes, add-ons, and updates, for instance, to its firmware, software (e.g., including executable instructions, applications, program modules), and operating system.

According to one embodiment, the sensor computing entity 102 may comprise location determining aspects, devices, modules, functionalities, and/or similar words used herein interchangeably. For example, the sensor computing entity 102 may comprise outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This information/data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the sensor computing entity's 102 position in connection with a variety of other systems, including cellular towers, Wi-Fi access points, and/or the like. Similarly, the sensor computing entity 102 may comprise indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may comprise the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The sensor computing entity 102 may also comprise a user interface (that can comprise a display 316 coupled to a processing element 308) and/or a user input interface (coupled to a processing element 308). For example, the user interface may be a user application, browser, user interface, and/or similar words used herein interchangeably executing on and/or accessible via the sensor computing entity 102 to interact with and/or cause display of information/data from the predictive data analysis computing entity 106, as described herein. The user input interface can comprise any of a number of devices or interfaces allowing the sensor computing entity 102 to receive data, such as a keypad 318 (hard or soft), a touch display, voice/speech or motion interfaces, or other input device. In embodiments including a keypad 318, the keypad 318 can comprise (or cause display of) the conventional numeric (0-9) and related keys (#, *), and other keys used for operating the sensor computing entity 102 and may comprise a full set of alphabetic keys or set of keys that may be activated to provide a full set of alphanumeric keys. In addition to providing input, the user input interface can be used, for example, to activate or deactivate certain functions, such as screen savers and/or sleep modes.

The sensor computing entity 102 can also comprise volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the sensor computing entity 102. As indicated, this may comprise a user application that is resident on the entity or accessible through a browser or other user interface for communicating with the predictive data analysis computing entity 106 and/or various other computing entities.

In another embodiment, the sensor computing entity 102 may comprise one or more components or functionality that are the same or similar to those of the predictive data analysis computing entity 106, as described in greater detail above. As will be recognized, these architectures and descriptions are provided for exemplary purposes only and are not limiting to the various embodiments.

In various embodiments, the sensor computing entity 102 may be embodied as an artificial intelligence (AI) computing entity, such as an Amazon Echo, Amazon Echo Dot, Amazon Show, Google Home, and/or the like. Accordingly, the sensor computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

Exemplary Augmented Reality Device

FIG. 4 provides an illustrative schematic representative of an augmented reality device 103 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. As shown in FIG. 4, the augmented reality device 103 can comprise an antenna 412, a transmitter 404 (e.g., radio), a receiver 406 (e.g., radio), and a processing element 408 (e.g., CPLDs, microprocessors, multi-core processors, coprocessing entities, ASIPs, microcontrollers, and/or controllers) that provides signals to and receives signals from the transmitter 404 and receiver 406, correspondingly.

The signals provided to and received from the transmitter 404 and the receiver 406, correspondingly, may comprise signaling information/data in accordance with air interface standards of applicable wireless systems. In this regard, the augmented reality device 103 may be capable of operating with one or more air interface standards, communication protocols, modulation types, and access types. More particularly, the augmented reality device 103 may operate in accordance with any of a number of wireless communication standards and protocols, such as those described above with regard to the predictive data analysis computing entity 106. In a particular embodiment, the augmented reality device 103 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the augmented reality device 103 may operate in accordance with multiple wired communication standards and protocols, such as those described above with regard to the predictive data analysis computing entity 106 via a network interface 420.

Via these communication standards and protocols, the augmented reality device 103 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The augmented reality device 103 can also download changes, add-ons, and updates, for instance, to its firmware, software (e.g., including executable instructions, applications, program modules), and operating system.

According to one embodiment, the augmented reality device 103 may comprise location determining aspects, devices, modules, functionalities, and/or similar words used herein interchangeably. For example, the augmented reality device 103 may comprise outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This information/data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the augmented reality device's 103 position in connection with a variety of other systems, including cellular towers, Wi-Fi access points, and/or the like. Similarly, the augmented reality device 103 may comprise indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may comprise the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The augmented reality device 103 may also comprise a user interface (that can comprise a display 416 coupled to a processing element 408) and/or a user input interface (coupled to a processing element 408). For example, the user interface may be a user application, browser, user interface, and/or similar words used herein interchangeably executing on and/or accessible via the augmented reality device 103 to interact with and/or cause display of information/data from the predictive data analysis computing entity 106, as described herein. The user input interface can comprise any of a number of devices or interfaces allowing the augmented reality device 103 to receive data, such as a keypad 418 (hard or soft), a touch display, voice/speech or motion interfaces, or other input device. In embodiments including a keypad 418, the keypad 418 can comprise (or cause display of) the conventional numeric (0-9) and related keys (#, *), and other keys used for operating the augmented reality device 103 and may comprise a full set of alphabetic keys or set of keys that may be activated to provide a full set of alphanumeric keys. In addition to providing input, the user input interface can be used, for example, to activate or deactivate certain functions, such as screen savers and/or sleep modes.

The augmented reality device 103 can also comprise volatile storage or memory 422 and/or non-volatile storage or memory 424, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the augmented reality device 103. As indicated, this may comprise a user application that is resident on the entity or accessible through a browser or other user interface for communicating with the predictive data analysis computing entity 106 and/or various other computing entities.

In another embodiment, the augmented reality device 103 may comprise one or more components or functionality that are the same or similar to those of the predictive data analysis computing entity 106, as described in greater detail above. As will be recognized, these architectures and descriptions are provided for exemplary purposes only and are not limiting to the various embodiments.

In various embodiments, the augmented reality device 103 may be embodied as an artificial intelligence (AI) computing entity, such as an Amazon Echo, Amazon Echo Dot, Amazon Show, Google Home, and/or the like. Accordingly, the augmented reality device 103 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

V. Exemplary System Operations

As described below, various embodiments of the present invention provide techniques for providing augmented reality assistance mode functionalities in a dynamically triggerable manner. The noted techniques improve the efficiency of augmented reality devices by removing the computationally expensive augmented reality assistance mode functionalities from a default operational mode of the augmented reality devices, while nevertheless minimizing the utility tradeoff resulting from this removal by ensuring that the augmented reality assistance mode functionalities can be enabled using automatic triggers. In doing so, various embodiments of the present invention increase the computational efficiency of augmented reality devices, reduce the number of computationally expensive operations performed on the noted devices, and make substantial technical contributions to the field of augmented reality computing.

FIG. 5 provides a block diagram of the software architecture of the augmented reality device 103. As depicted in FIG. 5, the augmented reality device 103 includes a communication module 501, an education module 502, an assessment module 503, an assistance module 504, and a diagnosis module 505.

The communication module 501 is configured to perform a set of augmented reality communication mode operations that are in turn configured to enable a set of augmented reality communication mode functionalities. In some embodiments, the set of augmented reality communication mode operations are configured to be performed during a default operational mode of the augmented reality device 103. In some embodiments, the augmented reality communication mode functionalities are configured to provide communicational guidelines to an end user profile of the augmented reality device 103. Examples of communicational guidelines include real-time emotional awareness guidelines, real-time speech transcription guidelines, real-time sign language detection guidelines, real-time communication prompts, and real-time contextual awareness guidelines. Exemplary embodiments of real-time emotional awareness guidelines, the real-time speech transcription guidelines, the real-time sign language detection guidelines, the real-time communication prompts, and the real-time contextual awareness guidelines are further described below.

In some embodiments, the set of augmented reality communication mode operations are configured to provide information about one or more detected interactive participant profiles associated with a current end-user physical environment of an end user of the augmented reality device 103. An interactive participant profile may, in some embodiments, be a detected individual with whom an end user associated with an end user profile of an augmented reality device is detected to be directly or indirectly interacting. In some embodiments, an interactive participant profile is determined based at least in part on face detections performed using a real-time video stream of the current end-user physical environment of the augmented reality device. In some embodiments, an interactive participant profile is determined based at least in part on data (e.g., calendar confirmation data, vehicle usage data, location tracking data, and/or the like) that describes participants of a particular event in a particular location that is associated with a current end-user physical environment of the augmented reality device. In some embodiments, a predictive data analysis computing entity may be configured to generate at least one of a predicted emotional state for an individual associated with an interactive participant profile and a predicted sign language translation for an individual associated with an interactive participant profile.

The real-time emotional awareness guidelines may be configured to provide information about detected emotional states of interactive participant profiles associated with a current end-user physical environment of an end user of the augmented reality device 103. For example, a real-time emotional awareness guideline may describe that a particular interactive participant profile is happy at a current moment. As another example, a real-time emotional awareness guideline may describe that a particular interactive participant profile is angry at a current moment. As yet another example, a real-time emotional awareness guideline may describe that a particular interactive participant profile is upset at a current moment. As a further example, a real-time emotional awareness guideline may describe that a particular interactive participant profile is disturbed at a current moment.

In some embodiments, a real-time emotional awareness guideline is determined based at least in part on a predicted emotional state for an interactive participant profile in current end-user physical environment of an end user of the augmented reality device 103. In some embodiments, the predicted emotional state describes an inferred emotional designation for a detected face of an individual associated with an interactive participant profile. In some embodiments, the predicted emotional state for an individual is determined (e.g., by a predictive data analysis computing entity that interacts with an augmented reality device) by first processing a real-time video stream of a current end-user physical environment of an end user using a face detection machine learning model (e.g., a convolutional neural network machine learning model) to detect a face associated with an interactive participant profile, and then processing the face using an emotion detection machine learning model (e.g., a supervised machine learning model that includes an image processing component) in order to generate the predicted emotional state of the individual associated with the interactive participant. In some of the noted embodiments, an emotion detection machine learning model is a trained machine learning model that is configured to process image/video data associated with a detected face of an individual in order to generate a predicted emotional state of the individual. Examples of inputs to an emotion detection machine learning model include a sequence of one or more image matrices (e.g., where each matrix value describes the color intensities of a pixel of a captured image), while outputs of an emotion detection machine learning model include a vector describing a predicted correlation value for each candidate emotional state of a set of candidate emotional states.

In some embodiments, the predicted emotional state for an individual is determined (e.g., by a predictive data analysis computing entity that interacts with an augmented reality device) by first processing a real-time video stream of a current end-user physical environment of an end user using a face landmark detection machine learning model (e.g., a convolutional neural network machine learning model) to detect one or more facial landmarks of the individual, then processing the real-time video stream to detect one or more posture indications for the individual, and then processing the facial landmarks and the posture indications using an emotion detection machine learning model (e.g., a supervised machine learning model) in order to generate the predicted emotional state of the individual associated with the interactive participant. In some of the noted embodiments, an emotion detection machine learning model is a trained machine learning model that is configured to process data associated with detected facial features and posture indications of an individual in order to generate a predicted emotional state of the individual. Examples of inputs to an emotion detection machine learning model include a vector describing properties of each facial landmark and/or a vector describing properties of each posture indication, while outputs of an emotion detection machine learning model include a vector describing a predicted correlation value for each candidate emotional state of a set of candidate emotional states.

An operational example of an emotional awareness guideline 600 is depicted in FIG. 6. As depicted in FIG. 6, the emotional awareness guideline 600 describes the predicted emotional state of an individual interacting with an end user of an augmented reality computing device. In particular, as depicted in FIG. 6, the emotional awareness guideline 600 describes that the depicted individual is associated with a predicted emotional state describing that the depicted individual is likely happy.

The real-time speech transcription guidelines may be configured to provide textual transcriptions of a set of conversations occurring in a current end-user physical environment of the end user of the augmented reality device 103, such as conversations deemed to involve the end user. In some embodiments, to generate the data described by the real-time speech transcription guidelines, a real-time voice stream associated with a current end-user physical environment is processed by a voice transcription machine learning model in order to generate inferred text data for a defined set of conversations occurring in a current end-user physical environment of the end user of the augmented reality device 103.

The real-time sign language detection guidelines may be configured to provide information about detected sign language translations of interactive participant profiles associated with a current end-user physical environment of an end user of the augmented reality device 103. A detected sign language translation may describe inferred sign language interpretations for hand movements of an individual associated with an interactive participant profile. In some embodiments, a detected sign language translation is determined by processing a real-time video stream associated with a current end-user physical environment of an end user profile of an augmented reality device in order to detect one or more hand movements for the end user profile, and then processing the detected hand movements using a sign language detection machine learning model. In some of the noted embodiments, the sign language detection machine learning model is a supervised machine learning model that is configured to process hand movement detections associated with an interactive participant profile in order to generate the predicted sign language translation of the noted hand movement detections. In some embodiments, the inputs to the sign language detection machine learning model describe a sequence of vectors each describing a particular hand movement in a sequence of hand movements, while the outputs of the sign language detection machine learning model include a text string describing text data associated with the predicted sign language translation.

The education module 502 is configured to perform a set of augmented reality education mode operations that are in turn configured to enable a set of augmented reality education mode functionalities. In some embodiments, the set of augmented reality communication mode operations are not configured to be performed during a default operational mode of the augmented reality device 103, and may in some embodiments be manually triggerable. In some embodiments, the augmented reality education mode functionalities are configured to provide educational guidelines to an end user profile of the augmented reality device 103. Examples of educational guidelines include speech command training guidelines, emotional detection training guidelines, and directional training guidelines.

The assessment module 503 is configured to perform a set of augmented reality assessment mode operations that are in turn configured to enable a set of augmented reality assessment mode functionalities. In some embodiments, the set of assessment reality communication mode operations are not configured to be performed during a default operational mode of the augmented reality device 103, and may in some embodiments be manually triggerable. In some embodiments, the augmented reality assessment mode functionalities are configured to assess progress of the end user based at least in part on end-user responses to at least one of speech commands, emotional detection quizzes/games, augmented eye contact target exercises, and direction understanding augmented reality games/exercises.

The assistance module 504 is configured to perform a set of augmented reality assistance mode operations that are in turn configured to enable a set of augmented reality assistance mode functionalities. In some embodiments, an augmented reality assistance mode functionality is a set of computer-implemented operations that are configured to cause an augmented reality device to provide instructions to an end user of the augmented reality device. For example, an augmented reality assistance mode functionality may describe a set of computer-implemented operations that are configured to cause an augmented reality device to present one or more augmented reality visualizations (e.g., one or more augmented reality notifications) corresponding one or more detected threats in a current end-user physical environment of the end user. For example, in some embodiments, a set of augmented reality assistance mode functionalities may be configured to, in response to determining that the assistance mode triggering need determination is an affirmative assistance mode triggering need determination, perform the following two operations: (i) determine, based at least in part on a real-time video stream and by utilizing a threat detection machine learning model, one or more detected threat indications for a current end-user physical environment of an end user profile of an augmented reality device, and (ii) cause the augmented reality device (e.g., by providing threat detection data to the augmented reality device) to present one or more augmented reality visualizations corresponding to the one or more detected threat indications.

In some embodiments, a set of augmented reality assistance mode functionalities may be configured to provide assistance to an end user of an augmented reality device to be aware of any potential fall scenarios and/or any potential collision scenarios in a current end-user physical environment of the corresponding end user. In some embodiments, a set of augmented reality assistance mode functionalities may be configured to provide assistance to an end user of an augmented reality device about fast approaching vehicles or other obstacles. In some embodiments, a set of augmented reality assistance mode functionalities may be configured to provide assistance to an end user of an augmented reality device about shallow grounds and/or higher surfaces in the pathway of the end user. In some embodiments, a set of augmented reality assistance mode functionalities may be triggered automatically, manually, or both in manners. For example, in some embodiments, a set of augmented reality assistance mode functionalities may be triggered in response to determining that the assistance mode triggering need determination is an affirmative assistance mode triggering need determination. As another example, in some embodiments, a set of augmented reality assistance mode functionalities may be triggered either manually or dynamically in response to determining that the assistance mode triggering need determination is an affirmative assistance mode triggering need determination.

In some embodiments, the detected threat indications described by augmented reality visualizations that are generated as a result of performing a set of augmented reality assistance mode functionalities may be determined based at least in part on a location map of the current end-user physical environment of the end user. In some embodiments, the detected threat indications described by augmented reality visualizations that are generated as a result of performing a set of augmented reality assistance mode functionalities may be determined based at least in part on a real-time video stream of the current end-user physical environment of the augmented reality device.

In some embodiments, the set of augmented reality assistance mode functionalities may be manually triggerable. In some embodiments, the set of augmented reality assistance mode functionalities may be automatically triggerable. In some embodiments, the set of augmented reality assistance mode functionalities may be both manually triggerable and automatically triggerable. Accordingly, various embodiments of the present invention provide techniques for providing augmented reality assistance mode functionalities in a dynamically triggerable manner. The noted techniques improve the efficiency of augmented reality devices by removing the computationally expensive augmented reality assistance mode functionalities from a default operational mode of the augmented reality devices, while nevertheless minimizing the utility tradeoff resulting from this removal by ensuring that the augmented reality assistance mode functionalities can be enabled using automatic triggers. In doing so, various embodiments of the present invention increase the computational efficiency of augmented reality devices, reduce the number of computationally expensive operations performed on the noted devices, and make substantial technical contributions to the field of augmented reality computing.

FIG. 7 is a flowchart diagram of an example process 700 for performing a set of augmented reality assistance mode functionalities using an automatic triggering mechanism. While the process 700 is described herein as being performed by the predictive data analysis computing entity 106, a person of ordinary skill in the relevant technology will recognize that the process 700 may be performed by any other computing entity, such as by a computing entity associated with the augmented reality device 103 and/or by a client computing entity.

The process 700 begins at step/operation 701 when the predictive data analysis computing entity 106 determines an environment familiarity prediction for the current end-user physical environment based at least in part on current location data associated with a current end-user physical environment of the augmented reality device and a real-time video stream of the current end-user physical environment of the augmented reality device. In some embodiments, determining the interaction-wise familiarity prediction comprises determining, based at least in part on the real-time video stream, one or more detected participant indications for the current end-user physical environment; determining whether the one or more detected participant indications comprise at least one familiar participant indication for the end user profile; and in response to determining that the one or more detected participant indications comprise the at least one familiar participant indication for the end user profile, determining an affirmative interaction-wise familiarity prediction. In some of the noted embodiments, determining the environment familiarity prediction based at least in part on the location-wise familiarity prediction and the interaction-wise familiarity prediction comprises determining whether at least one of the location-wise familiarity prediction and the interaction-wise familiarity prediction describes an affirmative familiarity prediction; and in response to determining that the at least one of the location-wise familiarity prediction and the interaction-wise familiarity prediction describes the affirmative familiarity prediction, determining that the environment familiarity prediction is an affirmative environment familiarity prediction.

In some embodiments, the environment familiarity prediction is an inferred prediction about whether a current end-user physical environment of an end user of an augmented reality device is deemed to be a familiar environment for the end user. In some embodiments, an affirmative environment familiarity prediction describes that a corresponding current end-user physical environment is deemed to be a familiar environment, while a negative environment familiarity prediction describes that a corresponding current end-user physical environment is deemed an unfamiliar physical environment. In some embodiments, the environment familiarity prediction is determined as an affirmative environment familiarity prediction if a determined location of the current end-user physical environment of the end user is deemed to be a familiar location (e.g., a location that is designated as a home location may be deemed to be a familiar location and thus, if a determined location of a current end-user physical environment of an end user is deemed to be the home location, then the current end-user physical environment may be associated with an affirmative environment familiarity prediction).

In some embodiments, the environment familiarity prediction is determined as an affirmative environment familiarity prediction if at least n (e.g., at least one) detected participants in the current end-user physical environment of the end user are deemed to be familiar participants (e.g., a participant that is designated as an immediate family member may be deemed to be a familiar participant and thus, if at least n determined participants of a current end-user physical environment of an end user are deemed to be familiar participants, then the current end-user physical environment may be associated with an affirmative environment familiarity prediction). In some embodiments, the environment familiarity prediction is determined as an affirmative environment familiarity prediction if at least one of the following two conditions satisfied: (i) if a determined location of the current end-user physical environment of the end user is deemed to be a familiar location, and (ii) if one or more detected participants in the current end-user physical environment of the end user are deemed to be familiar participants. In some embodiments, the environment familiarity prediction is determined as an affirmative environment familiarity prediction if at least one of the following two conditions satisfied: (i) if a determined location of the current end-user physical environment of the end user is deemed to be a familiar location, and (ii) if at least n detected participants in the current end-user physical environment of the end user are deemed to be familiar participants. In some embodiments, the environment familiarity prediction for a current end-user physical environment of an end user is determined based at least in part on at least one of the following: (i) data describing designated location regions that are deemed to be familiar location regions for the end user, and (ii) data describing designated participant profiles that are deemed to be familiar participants for the end user.

In some embodiments, the environment familiarity prediction is determined based at least in part on a location-wise familiarity prediction, which may be an inferred prediction about whether a location designation of a current end-user physical environment of an end user of an augmented reality device is deemed to be a familiar location for the end user. In some embodiments, an affirmative location-wise familiarity prediction describes that a corresponding location designation of a current end-user physical environment is deemed to be a familiar location, while a negative location-wise familiarity prediction describes that a corresponding location designation of a current end-user physical environment is deemed to be an unfamiliar location. In some embodiments, the location-wise familiarity prediction for a current end-user physical environment is determined based at least in part on location data associated with the current physical environment, where the location data are configured to identify absolute coordinates and/or relative coordinates for a designated location of the current physical environment. Examples of location data include Global Positioning System (GPS) data. In some embodiments, a predicted environment familiarity prediction for a current end-user physical environment is determined based at least in part on a location-wise familiarity prediction and an interaction-wise familiarity prediction.

In some embodiments, determining an environment familiarity prediction based a location-wise familiarity prediction and an interaction-wise familiarity prediction comprises: determining whether at least one of the location-wise familiarity prediction and the interaction-wise familiarity prediction describes an affirmative familiarity prediction; and in response to determining that the at least one of the location-wise familiarity prediction and the interaction-wise familiarity prediction describes the affirmative familiarity prediction, determining that the environment familiarity prediction is an affirmative environment familiarity prediction.

In some embodiments, the environment familiarity prediction is determined based at least in part on an interaction-wise familiarity prediction, which may be an inferred prediction about whether at least n detected participants in a current end-user physical environment of an end user of an augmented reality device are deemed to be familiar individuals to the end user. In some embodiments, an affirmative interaction-wise familiarity prediction describes that at least n detected participants of a current end-user physical environment are deemed to be familiar individuals, while a negative location-wise familiarity prediction describes that less than n detected participants of a current end-user physical environment are deemed to be familiar individuals. In some embodiments, the interaction-wise familiarity prediction for a current end-user physical environment is determined based at least in part on detected faces in the current physical environment, such as detected faces determined based at least in part on performing image/video analysis on a current video stream of the current physical environment. In some embodiments, determining an environment familiarity prediction based a location-wise familiarity prediction and an interaction-wise familiarity prediction comprises: determining whether at least one of the location-wise familiarity prediction and the interaction-wise familiarity prediction describes an affirmative familiarity prediction; and in response to determining that the at least one of the location-wise familiarity prediction and the interaction-wise familiarity prediction describes the affirmative familiarity prediction, determining that the environment familiarity prediction is an affirmative environment familiarity prediction.

At step/operation 702, the predictive data analysis computing entity 106 determines an assistance mode triggering need determination for the augmented reality assistance mode functionalities based at least in part on the environment familiarity prediction. In some embodiments, determining the assistance mode triggering need determination comprises determining, based at least in part on a current physiological data stream associated with the end-user profile, a physiological condition severity prediction for the end-user profile; and determining the assistance mode triggering need determination based at least in part on the physiological condition severity prediction and the environment familiarity prediction. In some of the noted embodiments, determining the assistance mode triggering need determination based at least in part on the physiological condition severity prediction and the environment familiarity prediction comprises determining whether at least one of the physiological condition severity prediction and the environment familiarity prediction describes an affirmative determination; and in response to determining that the at least one of the physiological condition severity prediction and the environment familiarity prediction describes the affirmative determination, determining that the assistance mode triggering need determination is an affirmative assistance mode triggering need determination.

In some embodiments, the assistance mode triggering need determination describes whether one or more augmented reality assistance mode functionalities of an augmented reality device should be automatically triggered. In some embodiments, an augmented reality device is associated with a set of augmented reality assistance mode functionalities that are configured to provide instructions to an end user profile of the augmented reality device about navigating the physical, sensory, and/or social challenges associated with a current end-user physical environment of the end user profile. In some of the noted embodiments, the aforementioned set of augmented reality assistance mode functionalities of the augmented reality device are automatically triggered upon satisfaction of at least one of a set of triggering conditions, where each triggering condition in the set of triggering conditions may be associated with one or more defined statically-defined triggering criteria and/or one or more defined dynamically-defined triggering criteria.

For example, in some embodiments, the triggering conditions for a set of augmented reality assistance mode functionalities may include (e.g., may consist of) a dynamically-defined triggering criterion that is satisfied whenever a current end-user physical environment of an end user profile of an augmented reality device is associated with an affirmative environment familiarity prediction. In some embodiments, the assistance mode triggering determination for a set of augmented reality assistance mode functionalities is deemed to be an affirmative assistance mode triggering determination if the assistance mode triggering determination describes that the set of augmented reality assistance mode functionalities should be automatically triggered, while the assistance mode triggering determination for a set of augmented reality assistance mode functionalities is deemed to be a negative assistance mode triggering determination if the assistance mode triggering determination describes that the set of augmented reality assistance mode functionalities should not be automatically triggered.

In some embodiments, the assistance mode triggering determination for a set of augmented reality assistance mode functionalities is set to an affirmative assistance mode triggering determination if a current end-user physical environment of an end user profile of a corresponding augmented reality device is associated with an affirmative environment familiarity prediction. In some embodiments, the assistance mode triggering determination for a set of augmented reality assistance mode functionalities is set to an affirmative assistance mode triggering determination if both of the following triggering criteria are satisfied: (i) a current end-user physical environment of an end user profile of a corresponding augmented reality device is associated with an affirmative environment familiarity prediction, and (ii) one or more other triggering criteria are satisfied. In some embodiments, the assistance mode triggering determination for a set of augmented reality assistance mode functionalities is set to an affirmative assistance mode triggering determination if either of the following triggering conditions is satisfied: (i) a current end-user physical environment of an end user profile of a corresponding augmented reality device is associated with an affirmative environment familiarity prediction, and (ii) one or more other triggering conditions are satisfied.

In some embodiments, the assistance mode triggering need determination is determined based at least in part on a physiological condition severity prediction, which may be an inferred prediction whether a determined physiological state of an end user of an augmented reality device is deemed to be a normal/regular physiological state. In some embodiments, the physiological condition severity prediction is an affirmative physiological condition severity prediction if the determined physiological state of the corresponding end user is deemed to be a normal/regular physiological state, while the physiological condition severity prediction is a negative physiological condition severity prediction if the determined physiological state of the corresponding end user is not deemed to be a normal/regular physiological state. In some embodiments, the physiological condition severity prediction for an end user is determined based at least in part on a current physiological data stream associated with the end-user profile, such as a current physiological stream that describes one or more biometric measurements and/or one or more physiological measurements associated with the end user (e.g., one or more heart rate measurements associated with the end user, one or more pulse rate measurements associated with the end user, one or more breathing rate measurements, one or more blood glucose level measurements, and/or the like). In some embodiments, the environment familiarity prediction for a current end-user physical environment of an end user of an augmented reality computing device is determined based at least in part on a physiological condition severity prediction for the end user. For example, in some embodiments, determining the assistance mode triggering need determination based at least in part on the physiological condition severity prediction and the environment familiarity prediction comprises: determining whether at least one of the physiological condition severity prediction and the environment familiarity prediction describes an affirmative determination; and in response to determining that the at least one of the physiological condition severity prediction and the environment familiarity prediction describes the affirmative determination, determining that the assistance mode triggering need determination is an affirmative assistance mode triggering need determination.

At step/operation 703, the predictive data analysis computing entity 106 determines whether the assistance mode triggering need determination is an affirmative assistance mode triggering need determination. At steps/operations 704-705, in response to determining that the assistance mode triggering need determination is an affirmative assistance mode triggering need determination, the predictive data analysis computing entity 106 determines, based at least in part on the real-time video stream and by utilizing a threat detection machine learning model, one or more detected threat indications for the current end-user physical environment; and causes the augmented reality device 103 to present one or more augmented reality visualizations corresponding to the one or more detected threat indications. At step/operation 706, in response to determining that the assistance mode triggering need determination is a negative assistance mode triggering need determination, the predictive data analysis computing entity 106 does not trigger the set of augmented reality assistance mode functionalities.

Returning to FIG. 5, the diagnosis module 505 is configured to perform a set of augmented reality diagnosis mode operations that are in turn configured to enable a set of augmented reality diagnosis mode functionalities. The set of augmented reality diagnosis mode functionalities are configured to determine a conditional severity score for the end user profile of the augmented reality device 103 based at least in part on responses of the end user to a set of questions/challenges posed by the augmented reality device 103.

In some embodiments, the set of augmented reality diagnosis mode operations include transmitting data that are used to generate a conditional severity measure. In some embodiments, a conditional severity score may be generated using the process 800 of FIG. 8. While the process 800 is described herein as being performed by the predictive data analysis computing entity 106, a person of ordinary skill in the relevant technology will recognize that the process 800 may be performed by any other computing entity, such as by a computing entity associated with the augmented reality device 103 and/or by a client computing entity.

The process 800 begins at step/operation 801 when the predictive data analysis computing entity 106 identifies a plurality of emotional detection vectors for a plurality of challenge responses, wherein the plurality of emotional detection vectors comprise one or more affirmative-labeled emotional detection vectors and one or more negative-labeled emotional detection vectors. In some embodiments, an emotional detection vector describes a set of responses to a set of challenges (e.g., a set of emotional detection challenges, where each emotional detection challenge may in some embodiments present an face visualization and seeks a user detection of the emotional detection for the face visualization) for an individual. In some embodiments, when an emotional detection vector describes a set of responses by an individual deemed to have a target condition (e.g., autism), the emotional detection vector is deemed an affirmative-labeled emotional detection vector. In some embodiments, when an emotional detection vector describes a set of responses by an individual deemed not to have a target condition (e.g., autism), the emotional detection vector is deemed a negative-labeled emotional detection vector.

At step/operation 802, the predictive data analysis computing entity 106 determines a centroid of a cluster of negative-labeled emotional detection vectors (referred to herein as a negative-labeled centroid). For example, as depicted in FIG. 9, the centroid 901 is determined for the cluster 902 of negative-labeled emotional detection vectors, which are associated with children without autism. In some embodiments, the cluster of negative-labeled emotional detection vectors is determined using a clustering algorithm, such as density-based spatial clustering of applications with noise (DBSCAN).

At step/operation 803, the predictive data analysis computing entity 106 determines a conditional severity score based at least in part on the distance measure for an end user profile based at least in part on a distance measure of the emotional detection vector for the end user profile and the centroid of negative-labeled emotional detection vectors. In some embodiments, the conditional severity score is determined using the operations of Equation 1:

$$S=\theta-\beta*\text{assessment\_score}+\epsilon \quad \text{Equation 1}$$

As described in Equation 1, $\theta$ is the distance measure, assessment_score is a score obtained by the end user profile via interacting with the assessment module 503, $\beta$ is a tuned/trained weight of the assessment_score, and $\epsilon$ is an irreducible error.

Thus, as described above, various embodiments of the present invention provide techniques for providing augmented reality assistance mode functionalities in a dynamically triggerable manner. The noted techniques improve the efficiency of augmented reality devices by removing the computationally expensive augmented reality assistance mode functionalities from a default operational mode of the augmented reality devices, while nevertheless minimizing the utility tradeoff resulting from this removal by ensuring that the augmented reality assistance mode functionalities can be enabled using automatic triggers. In doing so, various embodiments of the present invention increase the computational efficiency of augmented reality devices, reduce the number of computationally expensive operations performed on the noted devices, and make substantial technical contributions to the field of augmented reality computing.

In some embodiments, as used throughout the present document, an "augmented reality device" includes an electronic device comprising at least one processor and memory that augments real world elements as presented to the user. Examples of an augmented reality device include augmented reality glasses, augmented reality headsets, and mobile devices including an augmented reality application. Examples of augmented reality devices further include mixed reality devices and virtual reality devices.

VI. Conclusion

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method for dynamically providing augmented reality assistance mode functionalities, the computer-implemented method comprising:

generating, by one or more processors and based at least in part on (a) current location data associated with a current end-user physical environment of an augmented reality device and (b) a real-time video stream of the current end-user physical environment, an environment familiarity prediction for the current end-user physical environment, wherein (a) the augmented reality device is associated with an end user profile, (b) the end-user profile comprises a conditional severity score associated with an end user, and (c) the conditional severity score is determined by:
 (i) identifying a plurality of emotional detection vectors for a plurality of challenge responses, wherein the plurality of emotional detection vectors comprises one or more affirmative-labeled emotional detection vectors and one or more negative-labeled emotional detection vectors,
 (ii) for each of the one or more affirmative-labeled emotional detection vector, determining a distance measure between the affirmative-labeled emotional detection vector and a negative-labeled centroid of the one or more negative-labeled emotional detection vectors, and
 (iii) determining the conditional severity score based at least in part on each determined distance measure;

determining, by the one or more processors and based at least in part on the environment familiarity prediction, an assistance mode triggering need for augmented reality assistance mode functionalities; and in response to determining that the assistance mode triggering need is an affirmative assistance mode triggering need:
(a) generating, by the one or more processors and by using a threat detection machine learning model, a threat indication prediction for the current end-user physical environment, wherein the threat indication prediction is based at least in part on the real-time video stream, and
(b) providing, by the one or more processors, the threat indication prediction to the augmented reality device to present using one or more augmented reality visualizations.

2. The computer-implemented method of claim 1, wherein generating the environment familiarity prediction comprises:
generating, based at least in part on the current location data, a location-wise familiarity prediction for the current end-user physical environment;
generating, based at least in part on the real-time video stream, an interaction-wise familiarity prediction for the current end-user physical environment; and
generating the environment familiarity prediction based at least in part on the location-wise familiarity prediction and the interaction-wise familiarity prediction.

3. The computer-implemented method of claim 2, wherein generating the interaction-wise familiarity prediction comprises:
determining, based at least in part on the real-time video stream, one or more detected participant indications for the current end-user physical environment;
determining whether the one or more detected participant indications comprise a familiar participant indication for the end user profile; and
in response to determining that the one or more detected participant indications comprise the familiar participant indication for the end user profile, generating an affirmative interaction-wise familiarity prediction.

4. The computer-implemented method of claim 2, wherein generating the environment familiarity prediction comprises:
determining whether at least one of the location-wise familiarity prediction or the interaction-wise familiarity prediction describes an affirmative familiarity prediction; and
in response to determining that at least one of the location-wise familiarity prediction or the interaction-wise familiarity prediction describes the affirmative familiarity prediction, determining that the environment familiarity prediction is an affirmative environment familiarity prediction.

5. The computer-implemented method of claim 1, wherein determining the assistance mode triggering need comprises:
generating, based at least in part on a current physiological data stream associated with the end-user profile, a physiological condition severity prediction for the end-user profile; and
determining the assistance mode triggering need based at least in part on the physiological condition severity prediction and the environment familiarity prediction.

6. The computer-implemented method of claim 5, wherein determining the assistance mode triggering need based at least in part on the physiological condition severity prediction and the environment familiarity prediction comprises:
determining whether at least one of the physiological condition severity prediction or the environment familiarity prediction describes an affirmative determination; and
in response to determining that the at least one of the physiological condition severity prediction or the environment familiarity prediction describes the affirmative determination, determining that the assistance mode triggering need is an affirmative assistance mode triggering need.

7. The computer-implemented method of claim 1, further comprising:
generating, based at least in part on the current real-time video stream and by using an emotion detection machine learning model, an emotional state prediction for an interactive participant profile in the current end-user physical environment; and
providing for the augmented reality device to present one or more second augmented reality visualizations corresponding to the emotional state prediction.

8. The computer-implemented method of claim 1, further comprising:
determining, based at least in part on the current real-time video stream and by using a sign language detection machine learning model, a sign language translation prediction for a set of recorded movements of an interactive participant profile in the current end-user physical environment; and
providing for the augmented reality device to present one or more second augmented reality visualizations corresponding to the sign language translation prediction.

9. An apparatus for dynamically providing augmented reality assistance mode functionalities to an end user profile of an augmented reality device, the apparatus comprising one or more processors and at least one memory including program code, the at least one memory and the program code configured to, with the one or more processors, cause the apparatus to at least:
determine, based at least in part on (a) current location data associated with a current end-user physical environment of an augmented reality device and (b) a real-time video stream of the current end-user physical environment, an environment familiarity prediction for the current end-user physical environment, wherein (a) the augmented reality device is associated with an end user profile, (b) the end-user profile comprises a conditional severity score associated with an end user, and (c) the conditional severity score is determined by:
(i) identifying a plurality of emotional detection vectors for a plurality of challenge responses, wherein the plurality of emotional detection vectors comprises one or more affirmative-labeled emotional detection vectors and one or more negative-labeled emotional detection vectors,
(ii) for each of the one or more affirmative-labeled emotional detection vectors, determining a distance measure between the affirmative-labeled emotional detection vector and a negative-labeled centroid of the one or more negative-labeled emotional detection vectors, and
(iii) determining the conditional severity score based at least in part on each determined distance measure;
generate, based at least in part on the environment familiarity prediction, an assistance mode triggering need for augmented reality assistance mode functionalities; and in response to determining that the assistance mode triggering need is an affirmative assistance mode triggering need:
- (a) generate, by using a threat detection machine learning model, a threat indication prediction for the current end-user physical environment, wherein the threat indication prediction is based at least in part on the real-time video stream, and
- (b) provide the threat indication prediction to the augmented reality device to present using one or more augmented reality visualizations.

10. The apparatus of claim 9, wherein generating the environment familiarity prediction comprises:
generating, based at least in part on the current location data, a location-wise familiarity prediction for the current end-user physical environment;
generating, based at least in part on the real-time video stream, an interaction-wise familiarity prediction for the current end-user physical environment; and
generating the environment familiarity prediction based at least in part on the location-wise familiarity prediction and the interaction-wise familiarity prediction.

11. The apparatus of claim 10, wherein generating the interaction-wise familiarity prediction comprises:
determining, based at least in part on the real-time video stream, one or more detected participant indications for the current end-user physical environment;
determining whether the one or more detected participant indications comprise a familiar participant indication for the end user profile; and
in response to determining that the one or more detected participant indications comprise the familiar participant indication for the end user profile, generating an affirmative interaction-wise familiarity prediction.

12. The apparatus of claim 10, wherein generating the environment familiarity prediction comprises:
determining whether at least one of the location-wise familiarity prediction or the interaction-wise familiarity prediction describes an affirmative familiarity prediction; and
in response to determining that at least one of the location-wise familiarity prediction or the interaction-wise familiarity prediction describes the affirmative familiarity prediction, determining that the environment familiarity prediction is an affirmative environment familiarity prediction.

13. The apparatus of claim 9, wherein determining the assistance mode triggering need comprises:
generating, based at least in part on a current physiological data stream associated with the end-user profile, a physiological condition severity prediction for the end-user profile; and
determining the assistance mode triggering need based at least in part on the physiological condition severity prediction and the environment familiarity prediction.

14. The apparatus of claim 9, wherein determining the assistance mode triggering need based at least in part on the physiological condition severity prediction and the environment familiarity prediction comprises:
determining whether at least one of the physiological condition severity prediction or the environment familiarity prediction describes an affirmative determination; and
in response to determining that the at least one of the physiological condition severity prediction or the environment familiarity prediction describes the affirmative determination, determining that the assistance mode triggering need is an affirmative assistance mode triggering need.

15. The apparatus of claim 9, wherein the at least one memory and the program code are configured to, with the one or more processors, cause the apparatus to at least:
generate, based at least in part on the current real-time video stream and by using an emotion detection machine learning model, an emotional state prediction for an interactive participant profile in the current end-user physical environment; and
provide for the augmented reality device to present one or more second augmented reality visualizations corresponding to the emotional state prediction.

16. The apparatus of claim 9, wherein the at least one memory and the program code are configured to, with the one or more processors, cause the apparatus to at least:
generate, based at least in part on the current real-time video stream and by using a sign language detection machine learning model, a sign language translation prediction for a set of recorded movements of an interactive participant profile in the current end-user physical environment; and
provide for the augmented reality device to present one or more second augmented reality visualizations corresponding to the sign language translation prediction.

17. A computer program product for dynamically providing augmented reality assistance mode functionalities to an end user profile of an augmented reality device, the computer program product comprising at least one non-transitory computer-readable storage medium having computer-readable program code portions stored therein, the computer-readable program code portions configured to:
determine, based at least in part on (a) current location data associated with a current end-user physical environment of an augmented reality device and (b) a real-time video stream of the current end-user physical environment, an environment familiarity prediction for the current end-user physical environment, wherein (a) the augmented reality device is associated with an end user profile, (b) the end-user profile comprises a conditional severity score associated with an end user, and (c) the conditional severity score is determined by:
- (i) identifying a plurality of emotional detection vectors for a plurality of challenge responses, wherein the plurality of emotional detection vectors comprises one or more affirmative-labeled emotional detection vectors and one or more negative-labeled emotional detection vectors,
- (ii) for each of the one or more affirmative-labeled emotional detection vector, determining a distance measure between the affirmative-labeled emotional detection vector and a negative-labeled centroid of the one or more negative-labeled emotional detection vectors, and
- (iii) determining the conditional severity score based at least in part on each determined distance measure;

generate, based at least in part on the environment familiarity prediction, an assistance mode triggering need for augmented reality assistance mode functionalities; and
in response to determining that the assistance mode triggering need is an affirmative assistance mode triggering need:
- (a) generate, by using a threat detection machine learning model, a threat indication prediction for the current end-user physical environment, wherein the threat indication prediction is based at least in part on the real-time video stream, and (b) provide the threat indication prediction to the augmented reality device to present using one or more augmented reality visualizations.

18. The computer program product of claim 17, wherein determining the environment familiarity prediction comprises:

generating, based at least in part on the current location data, a location-wise familiarity prediction for the current end-user physical environment;

generating, based at least in part on the real-time video stream, an interaction-wise familiarity prediction for the current end-user physical environment; and generating the environment familiarity prediction based at least in part on the location-wise familiarity prediction and the interaction-wise familiarity prediction.

* * * * *

UNITED STATES PATENT AND TRADEMARK OFFICE
CERTIFICATE OF CORRECTION

PATENT NO. : 11,663,790 B2
APPLICATION NO. : 17/405583
DATED : May 30, 2023
INVENTOR(S) : Kartik Chaudhary et al.

It is certified that error appears in the above-identified patent and that said Letters Patent is hereby corrected as shown below:

In the Claims

In Column 32, Line 57, Claim 1, delete "vector," and insert -- vectors, --, therefor.

In Column 34, Line 5, Claim 6, delete "that the" and insert -- that --, therefor.

In Column 35, Line 65, Claim 14, delete "that the" and insert -- that --, therefor.

In Column 36, Line 52, Claim 17, delete "vector," and insert -- vectors, --, therefor.

Signed and Sealed this
Fifth Day of September, 2023

Katherine Kelly Vidal
*Director of the United States Patent and Trademark Office*